US006468745B1

(12) United States Patent
Fitzmaurice et al.

(10) Patent No.: US 6,468,745 B1
(45) Date of Patent: Oct. 22, 2002

(54) METHOD FOR EXPRESSING A LIBRARY OF NUCLEIC ACID SEQUENCE VARIANTS AND SELECTING DESIRED TRAITS

(75) Inventors: Wayne P. Fitzmaurice; John A. Lindbo; Hal S. Padgett; Gregory P. Pogue, all of Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 0 days.

(21) Appl. No.: 09/359,304

(22) Filed: Jul. 21, 1999

Related U.S. Application Data

(63) Continuation-in-part of application No. 09/232,170, filed on Jan. 15, 1999, now abandoned, which is a continuation-in-part of application No. 09/008,186, filed on Jan. 16, 1998.

(51) Int. Cl.⁷ ............................ C12Q 1/68; C12N 15/09; C12N 15/64; C12N 5/00; C07H 21/04
(52) U.S. Cl. .................... 435/6; 435/69.1; 435/91.4; 435/410; 435/5; 435/468; 435/440; 435/235.1; 435/441; 435/446; 536/23.1
(58) Field of Search ...................... 435/5, 69.1, 6, 435/91.4, 410, 235.1, 414, 468, 440, 441, 446; 536/23.1; 530/350

(56) References Cited

U.S. PATENT DOCUMENTS

| | | |
|---|---|---|
| 4,885,248 A | 12/1989 | Ahlquist |
| 5,316,931 A | 5/1994 | Donson et al. |
| 5,466,788 A | 11/1995 | Ahlquist et al. |
| 5,491,076 A | 2/1996 | Carrington et al. |
| 5,500,360 A | 3/1996 | Ahlquist et al. |
| 5,589,367 A | 12/1996 | Donson et al. |
| 5,602,242 A | 2/1997 | Ahlquist et al. |
| 5,627,060 A | 5/1997 | Ahlquist et al. |
| 5,629,175 A | 5/1997 | Goodman et al. |
| 5,633,447 A | 5/1997 | Ahlquist et al. |
| 5,714,313 A | 2/1998 | Garfinkel et al. |
| 5,716,802 A | 2/1998 | Sijmons et al. |
| 5,723,755 A | 3/1998 | Fortin |
| 5,811,238 A | 9/1998 | Stemmer et al. |
| 5,811,653 A | 9/1998 | Turpen |
| 5,837,458 A | 11/1998 | Minshull et al. |
| 5,866,785 A | 2/1999 | Donson et al. |
| 5,898,097 A * | 4/1999 | Beachy et al. ............... 800/279 |
| 5,977,438 A | 11/1999 | Turpen et al. |

FOREIGN PATENT DOCUMENTS

| | | |
|---|---|---|
| WO | WO 94/10329 | 5/1994 |
| WO | WO 98/13487 | 4/1998 |
| WO | WO 98/27230 | 6/1998 |
| WO | WO 98/31837 | 7/1998 |
| WO | WO 99/36516 | 7/1999 |
| WO | WO 99/50429 | 10/1999 |

OTHER PUBLICATIONS

Evans, et al. Virology 141: 275–282, 1985.*
Ahlquist, et al., "Complete Nucleotide Sequence of Brome Mosaic Virus RNA3," *J. Mol. Biol.* 153–23–38 (1981).
Ahlquist, D., et al., "Multicomponent RNA plant virus infection derived from cloned viral cDNA," *Proc. Natl. Acad. Sci. USA* 81:7066–7070 (1984).
Arkin, et al., *Proc. Natl. Acad. Sci. USA* 89:7811–7815 (1992).
Arnold, "Design by Directed Evolution," *Acc. Chem. Res.* 31:125–131 (1998).
Black, et al., *Proc. Natl. Acad.. Sci. USA* 93:3525–3529 (1996).
Cadwell, et al., *PCR Methods App.* 3:S136–40 (1994).
Cadwell, et al., *PCR Methods App.* 2:28–33 (1992).
Christians, et al., "Directed evolution of thymidine kinase for AZT phosphorylation using DNA family shuffling", *Nat. Biotechnol.* 17:259–264 (1999).
Cleland, et al. *Protein Engineering: Principles and Practice*, Wiley–Liss (1996).
Crameri, A., et al., "Improved Green Fluorescent Protein by Molecular Evolution Using DNA Shuffling," *Nature Biotech.* 14:315–319 (1996).
Crameri, A., et al., "Molecular evolution of an arsenate detoxification pathway by DNA shuffling," *Nature Biotech.* 15:436:438 (1997).
Crameri, et al., "DNA shuffling of a family of genes from diverse species accelerates directed evolution," *Nature* 391:288–291.
Dawson, et al., "cDNA cloning of the complete genome of tobacco mosaic virus and production of infectious transcripts," *Proc. Natl. Acad. Sci. USA* 83:1832–1836 (1986).
Delagrave, et al., *Biotechnology* 11:1548–1552 (1993).
Deom, et al., "The 30–Kilodalton Gene Product of Tobacco Mosaic Virus Potentiates Virus Movement," *Science* 237:389–394 (1987).
Dijkstra, et al., *Practical Plant Virology: Protocols and Exercises*, Springer Verlag (1998).
*DNA Cloning*, D.M. Clover, Ed., IRL Press, Oxford (1985).
Donson, et al., "Agrobacterium–Mediated Infectivity of Cloned Digitaria Streak Virus DNA," *Virology* 162:248–250 (1988).
Eckert, et al., *PCR Methods App.* 1:17–24 (1991).
Elmer, et al., "Agrobacterium–mediated inoculation of plants with tomato golden mosaic virus DNAs," *Plant Mol. Biol.* 10:225–234 (1988).
Fukuda, et al., "The Site of Initiation of Rod Assembly on the RNA of a Tomato and a Cowpea Strain of Tobacco Mosaic Virus," *Virology* 101:493–502 (1980).

(List continued on next page.)

Primary Examiner—David Guzo
Assistant Examiner—Gerald G. Leffers, Jr.
(74) Attorney, Agent, or Firm—Albert P. Halluin; Thomas Gallegos; Robin C. Chiang

(57) ABSTRACT

The present invention relates to a method for using viral vectors to bear populations of sequence variants and using plant hosts to select the sequences that exhibit the desired traits.

25 Claims, No Drawings

OTHER PUBLICATIONS

Gardiner, et al., "Genetic analysis of tomato golden mosaic virus: the coat protein is not required for systemic spread of symptom development," *EMBO J.* 7(4):899–904 (1988).

Gardner, et al., "Potato spindle tuber viroid infections mediated by the Ti plasmid of *Agrobacterium tumefaciens*," *Plant. Mol. Biol.* 6:221–228 (1986).

Giver, et al., ibid 2:335–338 (1998).

Graham, et al., "Wound–induced Proteinase Inhibitors from Tomato Leaves," *J. Biol. Chem.* 260(11):6555–6560 (1985).

Gramm, et al., *Proc. Natl. Acad. Sci. USA* 89:3576–3580 (1992).

Grimsley, et al., "Agroinfection," an alternative route for viral infection of plants by using the Ti plasmid, *Proc. Natl. Acad. Sci.* USA 83:3282–3286 (1986).

Grimsley, et al., "Agrobacterium–mediated delivery of infectious maize streak virus into maize plants," *Nature* 325:177–179 (1987).

Hayes, et al., "Agroinfection of *Triticum aestivum* with Cloned DNA of Wheat Dwarf Virus," *J. Gen. Virol.* 69:891–896 (1988).

Isaksson and Landegren, *Curr. Opinion Biotechnology* 10:11–15 (1999).

Kuchner, et al., *Trends Biotechnol.* 15:523–530 (1997).

Kurisu, et al., "Biochemical Characterization of Cucumber Green Mottle Mosaic Virus Ribonucleic Acid," *Virology* 70:214–216 (1976).

Lazarowitz, S., "Infectivity and complete nucleotide sequence of the genome of a Sough African isolate of maize streak virus," *Nucl. Acids Res.* 16(1):229–249 (1988).

Lebeurier, et al., "Inside–out model for self–assembly of tobacco mosaic virus," *Proc. Natl. Acad. Sci. USA* 74:149–153 (1977).

Lopato, S., et al., "Characterization of a Novel Arginine/Serine–Rich Splicing Factor in Arabidopsis," *The Plant Cell* 8:2255–2264 (1996).

Lopez, A., "Alternative Splicing of Pre–mRNA: Development Consequences and Mechanisms of Regulation," *Annu. Rev. Genetics* 32:279–305 (1998).

Matthews, *Plant Virology*, 3rd Ed. Academic Press, San Diego (1991).

Meshi, et al., "Nucleotide Sequence of the Coat Protein Cistron and the 3' Noncoding Region of Cucumber Green Mottle Mosaic Virus (Watermelon Strain) RNA," *Virology* 127:54–64 (1983).

*Methods in Enzymol* Vols. 68, 100, 101, 118, and 152–155) (1979, 1983, 1986 and 1987).

Miller, W. and Hall, T., "RNA–Dependent RNA Polymerase Isolated from Cowpea Chlorotic Mottle Virus–Infected Cowpeas Is Specific for Bromoviral RNA," *Virology* 132:53–60 (1984).

Minshull, et al., "Protein evolution by molecular breeding," *Curr. Opin. Chem. Biol.* 3:284–290 (1999).

Moore, et al., "Directed evolution of a para–nitrobenzyl esterase for aqueous–organic solvents," *Natl. Biotechnol.* 14:458–467 (1996).

Nagar, et al., "A Geminivirus Induces Expression of a Host DNA Synthesis Protein in Terminally Differentiated Plant Cells," *The Plant Cell*, 7:705–719 (1995).

Nozu, et al., "Chemical and Immunological Characterization of Cucumber Green Mottle Mosaic Virus (Watermelon Strain Protein)," *Virology* 45:577–585 (1971).

Ooshika, I., et al., "Identification of the 30K Protein of TMV by Immunoprecipitation with Antibodies Directed against a Synthetic Peptide," *Virology* 132:71 (1984).

Patten, et al., "Applications of DNA shuffling to pharmaceuticals and vaccines," *Curr. Opin. Chem. Biol.* 8:724–733 (1997).

*Plant Virology Protocol: From Virus Isolation to Transgenic Resistance in Methods in Molecular Biology*, vol. 81, Foster and Taylor, Ed., Humana Press (1998).

Sambrook, et al., *Molecular Cloning: A Laboratory Manual*, Second Edition, Cold Spring Harbor Labortory Press, Plainview, NY (1982, 1989).

Schwechheimer, C., et al., "Plant Transcription Factor Studies," *Annu. Rev. Plant Physiol. Plant Mol. Biol.* 49:127–150 (1998).

Shao, et al., "Random–priming *in vitro* recombination: an effective tool for directed evolution," *Nucleic Acids Res* 26:681–683 (1998).

Stemmer, "Rapid evolution of a protein *in vitro* by a DNA shuffling," *Nature* 370:389–391 (1994).

Stemmer, "DNA shuffling by random fragmentation and reassembly: *In vitro* recombination for molecular evolution," *Proc. Natl. Acad. Sci. USA* 91:10747–10751 (1994).

Stemmer, *Sexual PCR and Assembly PCR in the Encyclopedia of Molecular Biology*, VCH Publishers, New York, pp. 447–457 (1996).

Turpen, et al., "Transfection of whole plants from wounds inoculated with *Agrobacterium tumefaciens* containing cDNA of tobacco mosiac virus," *J. Virol. Methods* 46:227–240 (1993).

You, et al., *Protein Eng.* 9:77–83 (1994).

Zhang, et al., "Directed evolution of a fucosidase from a galactosidase by DNA shuffling and screening," *Proc. Natl. Acad. Sci. USA* 94:4504–4509 (1997).

Zhao, et al., "Functional and nonfunctional mutations distinguished by random recombination of homologous genes," *Proc. Natl. Acad. Sci. USA* 94:797–8000 (1997).

Zhao, et al., "Molecular evolution by staggered extension process (StEP) in vitro recombination," *Nat. Biotechnol.* 16:258–261 (1998).

Zhao, et al., "Directed evolution converts subtilisin E into a functional equivalent of thermitase," *Protein Eng.* 12:47–53 (1999).

* cited by examiner

METHOD FOR EXPRESSING A LIBRARY OF NUCLEIC ACID SEQUENCE VARIANTS AND SELECTING DESIRED TRAITS

This application is a Continuation-In-Part application of U.S. patent application Ser. No. 09/232,170, filed on Jan. 15, 1999, now abandoned, which is a Continuation-In-Part application of U.S. patent application Ser. No. 09/008,186, filed on Jan. 16, 1998.

FIELD OF THE INVENTION

The present invention relates generally to the field of molecular biology and viral genetics. Specifically, the present invention relates to a method for using viral vectors to house populations of nucleic acid sequence variants and to select one or more sequences that exhibit the desired traits using plant hosts.

BACKGROUND OF THE INVENTION

Nature has developed many strategies for generating genetic diversity over billions of years of evolution. These strategies include random mutagenesis, recombination and selection. Many methods are now available in the laboratory to mimic these processes in order to efficiently generate beneficial mutations and select molecules with desired traits. For recent reviews, see Minshull et al., *Curr. Opin. Chem. Biol.* 3:284–290 (1999); Giver et al., ibid 2:335–338 (1998); and Patten et al., ibid 8:724–733 (1997).

The generation of genetic diversity through in vitro recombination methods is often referred to as "molecular breeding" or "directed evolution" (Minshull et al., supra and Kuchner et al., *Trends Biotechnol.* 15:523–530 (1997)). DNA shuffling is a method for generating, in vitro, recombinant genes from a set of parent genes (Stemmer, *Nature*, 370:389–391 (1994); Stemmer, *Proc. Natl. Acad. Sci. USA* 91:10747–10751 (1994); Crameri et al., *Nat. Biotechnol.* 14:315–319 (1996); Crameri et al., *Nature Medicine* 2:100–103 (1996); Stemmer, *Sexual PCR and Assembly PCR* in *The Encyclopedia of molecular Biology*, VCH Publishers, New York, pp. 447–457 (1996); Crameri et al., *Nat. Biotechnol.* 15:436–438 (1997); Zhang et al., *Proc. Natl. Acad. Sci. USA* 94:4504–4509 (1997); Crameri et al., *Nature* 391:288–291 (1998); Christians et al., *Nat. Biotechnol.* 17:259–264 (1999), U.S. Pat. Nos. 5,830,721, 5,811,238, 5,830,721, 5,605,793, 5,834,252, and 5,837,458; and PCT publications WO 98/13487, WO98/27230, and WO 98/31837). Typically, the parental genes are randomly fragmented by Dnase I. The purified fragments are then reassembled by repeated cycles of overlap extension into full-length genes that contain novel combinations of the parental mutations.

Other in vitro recombination methods have also been developed to generate a population of nucleic acid sequences, for example, random priming recombination (RPR) and the staggered extension process (StEP) (Moore et al., *Nat. Biotechnol.* 14:458–467 (1996); Zhao et al., *Proc. Natl. Acad. Sci. USA* 94:7997–8000 (1997); Arnold, *Acc. Chem. Res.* 31:125–131 (1998); Shao et al., *Nucleic Acids Res.* 26:681–683 (1998); Zhao et al., *Nat. Biotechnol.* 16:258–261 (1998); Arnold, *Proc. Natl. Acad. Sci. USA* 95:2035–2036 (1998); Giver et al., *Proc. Natl. Acad. Sci. USA* 95:12809–12813 (1998); and Zhao et al., *Protein Eng.* 12:47–53 (1999)). In the RPR method, short random primers are annealed to the template and extended by polymerase. The resulting fragments, the length of which can be controlled by altering the conditions of the annealing and extension reaction, are then separated from the initial template and unextended primers. These fragments are assembled into full length genes by cycles of overlap extension. The StEP method uses template switching during synthesis to form the desired chimeric genes. The templates are mixed with one or more primers and subjected to repeated cycles of denaturation and short annealing/extension steps. Because the growing fragments can anneal to different templates, the resulting full length sequences contain sequence information from different parents.

DNA shuffling and other in vitro recombination methods have been applied to prokaryotic or cell-base systems to select sequences of desired protein activities. However, the ability to introduce sequence variants throughout an organism in a rapid and high throughput manner has not been demonstrated. Virus vectors are ideal for shuttling libraries of sequence variants throughout an organism, such as plants, for selection of optimized functions. No other tool, transient or stable expression methods, can match the ability of viral vectors to develop optimized functions using plant hosts.

Viruses are a unique class of infectious agents whose distinctive features are their simple organization and their mechanism of replication. Their hosts include a wide variety of plants and animals. A complete viral particle, or virion, may be regarded mainly as a block of genetic material (either DNA or RNA) capable of autonomous replication, surrounded by a protein coat and sometimes by an additional membranous envelope. The coat protects the virus from the environment and serves as a vehicle for transmission from one host cell to another.

Foreign genes can be expressed in plant hosts either by permanent insertion into the genome or by transient expression using virus-based vectors. Each approach has its own distinct advantages. Transformation for permanent expression needs to be done only once, whereas each generation of plants needs to be inoculated with the transient expression vector. Virus-based expression systems, in which the foreign mRNA is greatly amplified by virus replication, can produce very high levels of proteins in leaves and other tissues. Viral vector-produced protein can also be directed to specific subcellular locations, such as endomembrane, cytosol, or organelles, or it can be attached to macromolecules, such as virions, which aids purification of the protein. For the production of some products, including products for the human health industry, plants provide an optimal system because of reduced capital costs and the greater potential for large-scale production compared with microbial or animal systems.

In this invention, we describe the use of viral expression vectors to bear populations of sequence variants. Plant hosts are used to select those sequences with desired properties, which may be further characterized.

SUMMARY OF THE INVENTION

The present invention is a method for selecting desired traits in a plant host by the use of viral vectors to express libraries of nucleic acid sequence variants. This in vitro evolution method is used to improve virus-specific, protein-specific, or host-specific functions. Libraries of sequence variants may be generated by in vitro mutagenesis and/or recombination methods, such as chemical treatment, oligonucleotide mediated mutagenesis, PCR mutagenesis, DNA shuffling, random priming recombination (RPR), restriction enzyme fragment induced template switching (REFITS), and the staggered extension process (StEP), among others. Libraries of sequence variants may be random, semi-random or known sequences. In preferred embodiments, RNA viral vectors may be used as the genetic backbones to bear libraries containing variants of nucleic acid sequences and to be applied to plant hosts such that the desired traits in the RNA or protein products can be determined, selected and improved. The template nucleic acid sequences for generating sequence variants may be of viral origin, such as, sequences encoding, coat protein, movement protein, promoter, internal initiation sites, packaging signals, 5' and 3' NTRs, or ribosomal sequences, or any other structural and non-structural components of viral nucleic acid sequences. The template nucleic acid sequences for generating sequence variants may also be derived from genes, regulatory sequences, or fragments thereof from bacteria, fungi, plants, animals or other sources. These non-native sequences may be inserted in viral vectors to express foreign proteins, regulate transcription or translation, increase the genetic stability of foreign sequences in viral vectors, etc.

After a plant host is infected with a library containing populations of sequence variants, one or more desired traits are screened and selected. The desired traits may include biochemical or phenotypic traits. Phenotypic traits may include, but not limited to, host range, viral infectivity, tolerance to herbicides, tolerance to extremes of heat or cold, drought, salinity or osmotic stress; resistance to pests (insects, nematodes or arachnids) or diseases (fungal, bacterial or viral), male or female sterility, dwarfness; early maturity, improved yield, vigor, heterosis, nutritional qualities, flavor or processing properties, and others. Biochemical traits may be related to, for example, promoter activities, transcription activities, translational activities, regulatory activities, movement activities (local and systemic), cellular signaling activities, extraction/purification properties, etc. The screening of sequence libraries is typically followed by rescue of the viruses from populations conferring desired traits. In some embodiments, re-screening of sub-libraries may become necessary. In other embodiments, sequences of the viral nucleic acids conferring desired traits may be determined and compared with the template sequences.

DETAILED DESCRIPTION OF THE INVENTION

The present invention relates to a method for using viral vectors to bear populations of sequence variants and using plant hosts to select the sequences that exhibit the desired traits.

I. Construction of Suitable Viral Vectors to House Libraries of Sequence Variants Viral vectors into which libraries of sequence variants are inserted may be constructed using a variety of methods known in the art. In preferred embodiments of the instant invention, the viral vectors used to bear libraries of sequence variants are derived from the RNA plant viruses. A variety of plant virus families may be used, such as Bromoviridae, Bunyaviridae, Comoviridae, Geminiviridae, Potyviridae, and Tombusviridae, among others. Within the plant virus families, various genera of viruses may be suitable for the instant invention, such as alfamovirus, ilarvirus, bromovirus, cucumovirus, tospovirus, carlavirus, caulimovirus, closterovirus, comovirus, nepovirus, dianthovirus, furovirus, hordeivirus, luteovirus, necrovirus, potexvirus, potyvirus, rymovirus, bymovirus, oryzavirus, sobemovirus, tobamovirus, tobravirus, carmovirus, tombusvirus, tymovirus, umbravirusa, and among others.

Within the genera of plant viruses, many species are particular preferred. They include alfalfa mosaic virus, tobacco streak virus, brome mosaic virus, broad bean mottle virus, cowpea chlorotic mottle virus, cucumber mosaic virus, tomato spotted wilt virus, carnation latent virus, caulflower mosaic virus, beet yellows virus, cowpea mosaic virus, tobacco ringspot virus, carnation ringspot virus, soil-borne wheat mosaic virus, tomato golden mosaic virus, cassava latent virus, barley stripe mosaic virus, barley yellow dwarf virus, tobacco necrosis virus, tobacco etch virus, potato virus X, potato virus Y, rice necrosis virus, ryegrass mosaic virus, barley yellow mosaic virus, rice ragged stunt virus, Southern bean mosaic virus, tobacco mosaic virus, ribgrass mosaic virus, cucumber green mottle mosaic virus watermelon strain, oat mosaic virus, tobacco rattle virus, carnation mottle virus, tomato bushy stunt virus, turnip yellow mosaic virus, carrot mottle virus, among others. In addition, RNA satellite viruses, such as tobacco necrosis satellite may also be employed.

A given plant virus may contain either DNA or RNA, which may be either single- or double-stranded. One example of plant viruses containing double-stranded DNA includes, but not limited to, caulimoviruses such as cauliflower mosaic virus (CaMV). Representative plant viruses which contain single-stranded DNA are cassava latent virus, bean golden mosaic virus (BGMV), and chloris striate mosaic virus. Rice dwarf virus and wound tumor virus are examples of double-stranded RNA plant viruses. Single-stranded RNA plant viruses include tobacco mosaic virus (TMV), turnip yellow mosaic virus (TYMV), rice necrosis virus (RNV) and brome mosaic virus (BMV). The single-stranded RNA viruses can be further divided into plus sense (or positive-stranded), minus sense (or negative-stranded), or ambisense viruses. The genomic RNA of a plus sense RNA virus is messenger sense, which makes the naked RNA infectious. Many plant viruses belong to the family of plus sense RNA viruses. They include, for example, TMV, BMV, and others. RNA plant viruses typically encode several common proteins, such as replicase/polymerase proteins essential for viral replication and MRNA synthesis, coat proteins providing protective shells for the extracellular passage, and other proteins required for the cell-to-cell movement, systemic infection and self-assembly of viruses. For general information concerning plant viruses, see Matthews, *Plant Virology,* 3$^{rd}$ Ed., Academic Press, San Diego (1991).

Selected groups of suitable plant viruses are characterized below. However, the invention should not be construed as limited to using these particular viruses, but rather the method of the present invention is contemplated to include all plant viruses at a minimum.

Tobamovirus Group

Tobacco Mosaic virus (TMV) is a member of the tobamoviruses. The TMV virion is a tubular filament, and comprises coat protein sub-units arranged in a single right-handed helix with the single-stranded RNA intercalated between the turns of the helix. TMV infects tobacco as well as other plants. TMV is transmitted mechanically and may remain infective for a year or more in soil or dried leaf tissue.

The TMV virions may be inactivated by subjection to an environment with a pH of less than 3 or greater than 8, or by formaldehyde or iodine. Preparations of TMV may be obtained from plant tissues by $(NH_4)_2SO_4$ precipitation, followed by differential centrifugation.

Tobacco mosaic virus (TMV) is a positive-stranded ssRNA virus whose genome is 6395 nucleotides long and is capped at the 5'-end but not polyadenylated. The genomic RNA can serve as mRNA for protein of a molecular weight of about 130,000 (130 K) and another produced by readthrough of molecular weight about 180,000 (180 K). However, it cannot function as a messenger for the synthesis of coat protein. Other genes are expressed during infection by the formation of monocistronic, 3'-coterminal subgenomic mRNAs, including one (LMC) encoding the 17.5 K coat protein and another (I$_2$) encoding a 30K protein. The 30K protein has been detected in infected protoplasts as described in Miller, J., *Virology* 132:71 (1984), and it is involved in the cell-to-cell transport of the virus in an infected plant as described by Deom et al., *Science* 237:389 (1987). The functions of the two large proteins are unknown, however, they are thought to function in RNA replication and transcription.

Several double-stranded RNA molecules, including double-stranded RNAs corresponding to the genomic, I$_2$ and LMC RNAs, have been detected in plant tissues infected with TMV. These RNA molecules are presumably intermediates in genome replication and/or mRNA synthesis processes which appear to occur by different mechanisms.

TMV assembly apparently occurs in plant cell cytoplasm, although it has been suggested that some TMV assembly may occur in chloroplasts since transcripts of ctDNA have been detected in purified TMV virions. Initiation of TMV assembly occurs by interaction between ring-shaped aggregates ("discs") of coat protein (each disc consisting of two layers of 17 subunits) and a unique internal nucleation site in the RNA; a hairpin region about 900 nucleotides from the 3'-end in the common strain of TMV. Any RNA, including subgenomic RNAs containing this site, may be packaged into virions. The discs apparently assume a helical form on interaction with the RNA, and assembly (elongation) then proceeds in both directions (but much more rapidly in the 3'- to 5'- direction from the nucleation site).

Another member of the Tobamoviruses, the Cucumber Green Mottle Mosaic virus watermelon strain (CGMMV-W) is related to the cucumber virus (Nozu et al., *Virology* 45:577 (1971)). The coat protein of CGMMV-W interacts with RNA of both TMV and CGMMV to assemble viral particles in vitro (Kurisu et al., *Virology* 70:214 (1976)).

Several strains of the tobamovirus group are divided into two subgroups, on the basis of the location of the origin of assembly. Subgroup I, which includes the vulgare, OM, and tomato strain, has an origin of assembly about 800–1000 nucleotides from the 3'-end of the RNA genome, and outside the coat protein cistron (Lebeurier et al., *Proc. Natl. Acad. Sci. USA* 74:149 (1977); and Fukuda et al., *Virology* 101:493 (1980)). Subgroup II, which includes CGMMV-W and cowpea strain (Cc) has an origin of assembly about 300–500 nucleotides from the 3'-end of the RNA genome and within the coat protein cistron. The coat protein cistron of CGMMV-W is located at nucleotides 176-661 from the 3'-end. The 3' noncoding region is 175 nucleotides long. The origin of assembly is positioned within the coat protein cistron (Meshi et al., *Virology* 127:54 (1983)).

Brome Mosaic Virus Group

Brome Mosaic virus (BMV) is a member of a group of tripartite, single-stranded, RNA-containing plant viruses commonly referred to as the bromoviruses. Each member of the bromoviruses infects a narrow range of plants. Mechanical transmission of bromoviruses occurs readily, and some members are transmitted by beetles. In addition to BMV, other bromoviruses include broad bean mottle virus and cowpea chlorotic mottle virus.

Typically, a bromovirus virion is icosahedral, with a diameter of about 26 μm, containing a single species of coat protein. The bromovirus genome has three molecules of linear, positive-sense, single-stranded RNA, and the coat protein mRNA is also encapsidated. The RNAs each have a capped 5'-end, and a tRNA-like structure (which accepts tyrosine) at the 3'-end. Virus assembly occurs in the cytoplasm. The complete nucleotide sequence of BMV has been identified and characterized as described by Ahlquist et al., *J. Mol. Biol.* 153:23 (1981).

Rice Necrosis Virus

Rice Necrosis virus is a member of the Potato Virus Y Group or Potyviruses. The Rice Necrosis virion is a flexuous filament comprising one type of coat protein (molecular weight about 32,000 to about 36,000) and one molecule of linear positive-sense single-stranded RNA. The Rice Necrosis virus is transmitted by *Polymyxa oraminis* (a eukaryotic intracellular parasite found in plants, algae and fungi).

Geminiviruses

Geminiviruses are a group of small, single-stranded DNA-containing plant viruses with virions of unique morphology. Each virion consists of a pair of isometric particles (incomplete icosahedral), composed of a single type of protein (with a molecular weight of about $2.7-3.4 \times 10^4$). Each geminivirus virion contains one molecule of circular, positive-sense, single-stranded DNA. In some geminiviruses (i.e., Cassava latent virus and bean golden mosaic virus) the genome appears to be bipartite, containing two single-stranded DNA molecules.

Potyviruses

Potyviruses are a group of plant viruses which produce polyprotein. A particularly preferred potyvirus is tobacco etch virus (TEV). TEV is a well characterized potyvirus and contains a positive-strand RNA genome of 9.5 kilobases encoding for a single, large polyprotein that is processed by three virus-specific proteinases. The nuclear inclusion protein "a" proteinase is involved in the maturation of several replication-associated proteins and capsid protein. The helper component-proteinase (HC-Pro) and 35-kDa proteinase both catalyze cleavage only at their respective C-termini. The proteolytic domain in each of these proteins is located near the C-terminus. The 35-kDa proteinase and HC-Pro derive from the N-terminal region of the TEV polyprotein.

The selection of the genetic backbone for the viral vectors of the instant invention may depend on the plant host used. The plant host may be a monocotyledonous or dicotyledonous plant, plant tissue, or plant cell. Typically, plants of commercial interest, such as food crops, seed crops, oil crops, ornamental crops and forestry crops are preferred. For example, wheat, rice, corn, potato, barley, tobacco, soybean canola, maize, oilseed rape, lilies, grasses, orchids, irises, onions, palms, tomato, the legumes, or Arabidopsis, can be used as a plant host. Host plants may also include those readily infected by an infectious virus, such as Nicotiana, preferably, *Nicotiana benthamiana*, or *Nicotiana clevelandii*.

One feature of the present invention is the use of plant viral nucleic acids which comprise one or more non-native nucleic acid sequences capable of being transcribed in a plant host. These nucleic acid sequences may be native nucleic acid sequences that occur in a host plant. Preferably, these nucleic acid sequences are non-native nucleic acid sequences that do not normally occur in a host plant. For example, the plant viral vectors may contain sequences from more than one virus, including viruses from more than one taxonomic group. The plant viral nucleic acids may also contain sequences from non-viral sources, such as foreign genes, regulatory sequences, fragments thereof from bacteria, fungi, plants, animals or other sources. These foreign sequences may encode commercially useful proteins, polypeptides, or fusion products thereof, such as enzymes, antibodies, hormones, pharmaceuticals, vaccines, pigments, antimicrobial polypeptides, and the like. Or they may be sequences that regulate the transcription or translation of viral nucleic acids, package viral nucleic acid, and facilitate systemic infection in the host, among others.

In some embodiments of the instant invention, the plant viral vectors may comprise one or more additional native or non-native subgenomic promoters which are capable of transcribing or expressing adjacent nucleic acid sequences in the plant host. These non-native subgenomic promoters are inserted into the plant viral nucleic acids without destroying the biological function of the plant viral nucleic acids using known methods in the art. For example, the CaMV promoter can be used when plant cells are to be transfected. The subgenomic promoters are capable of functioning in the specific host plant. For example, if the host is tobacco, TMV, tomato mosaic virus, or other viruses containing subgenomic promoter may be utilized. The inserted subgenomic promoters should be compatible with the TMV nucleic acid and capable of directing transcription or expression of adjacent nucleic acid sequences in tobacco. It is specifically contemplated that two or more heterologous non-native subgenomic promoters may be used. The non-native nucleic acid sequences may be transcribed or expressed in the host plant under the control of the subgenomic promoter to produce the products of the nucleic acids of interest.

In some embodiments of the instant invention, the recombinant plant viral nucleic acids may be further modified by conventional techniques to delete all or part of the native coat protein coding sequence or put the native coat protein coding sequence under the control of a non-native plant viral subgenomic promoter. If it is deleted or otherwise inactivated, a non-native coat protein coding sequence is inserted under control of one of the non-native subgenomic promoters, or optionally under control of the native coat protein gene subgenomic promoter. Thus, the recombinant plant viral nucleic acid contains a coat protein coding sequence, which may be native or a nonnative coat protein coding sequence, under control of one of the native or non-native subgenomic promoters. The native or non-native coat protein gene may be utilized in the recombinant plant viral nucleic acid. The non-native coat protein, as is the case for the native coat protein, may be capable of encapsidating the recombinant plant viral nucleic acid and providing for systemic spread of the recombinant plant viral nucleic acid in the host plant.

In some embodiments of the instant invention, recombinant plant viral vectors are constructed to express a fusion between a plant viral coat protein and the foreign genes or polypeptides of interest. Such a recombinant plant virus provides for high level expression of a nucleic acid of interest. The location(s) where the viral coat protein is joined to the amino acid product of the nucleic acid of interest may be referred to as the fusion joint. A given product of such a construct may have one or more fusion joints. The fusion joint may be located at the carboxyl terminus of the viral coat protein or the fusion joint may be located at the amino terminus of the coat protein portion of the construct. In instances where the nucleic acid of interest is located internal with respect to the 5' and 3' residues of the nucleic acid sequence encoding for the viral coat protein, there are two fusion joints. That is, the nucleic acid of interest may be located 5', 3', upstream, downstream or within the coat protein. In some embodiments of such recombinant plant viruses, a "leaky" start or stop codon may occur at a fusion joint which sometimes does not result in translational termination.

In some embodiments of the instant invention, nucleic sequences encoding reporter protein(s) or antibiotic/herbicide resistance gene(s) may be constructed as carrier protein(s) for the polypeptides of interest, which may facilitate the detection of polypeptides of interest. For example, green fluorescent protein (GFP) may be simultaneously expressed with polypeptides of interest. In another example, a reporter gene, β-glucuronidase (GUS) may be utilized. In another example, a drug resistance marker, such as a gene whose expression results in kanamycin resistance, may be used.

Since the RNA genome is typically the infective agent, the cDNA is positioned adjacent a suitable promoter so that the RNA is produced in the production cell. The RNA is capped using conventional techniques, if the capped RNA is the infective agent. In addition, the capped RNA can be packaged in vitro with added coat protein from TMV to make assembled virions. These assembled virions can then be used to inoculate plants or plant tissues. Alternatively, an uncapped RNA may also be employed in the embodiments of the present invention. Contrary to the practiced art in scientific literature and in issued patent (Ahlquist et al., U.S. Pat. No. 5,466,788), uncapped transcripts for virus expression vectors are infective on both plants and in plant cells. Capping is not a prerequisite for establishing an infection of a virus expression vector in plants, although capping increases the efficiency of infection. In addition, nucleotides may be added between the transcription start site of the promoter and the start of the cDNA of a viral nucleic acid to construct an infectious viral vector. One or more nucleotides may be added. In some embodiments of the present invention, the inserted nucleotide sequence may contain a G at the 5'-end. Alternatively, the inserted nucleotide sequence may be GNN, GTN, or their multiples, $(GNN)_x$ or $(GTN)_x$.

In some embodiments of the instant invention, more than one nucleic acid is prepared for a multipartite viral vector construct. In this case, each nucleic acid may require its own origin of assembly. Each nucleic acid could be prepared to contain a subgenomic promoter and a non-native nucleic acid. Alternatively, the insertion of a non-native nucleic acid into the nucleic acid of a monopartite virus may result in the creation of two nucleic acids (i.e., the nucleic acid necessary for the creation of a bipartite viral vector). This would be advantageous when it is desirable to keep the replication and transcription or expression of the nucleic acid of interest separate from the replication and translation of some of the coding sequences of the native nucleic acid.

The recombinant plant viral nucleic acid may be prepared by cloning a viral nucleic acid. If the viral nucleic acid is DNA, it can be cloned directly into a suitable vector using conventional techniques. One technique is to attach an origin of replication to the viral DNA which is compatible with the cell to be transfected. In this manner, DNA copies of the chimeric nucleotide sequence are produced in the transfected cell. If the viral nucleic acid is RNA, a DNA copy of the viral nucleic acid is first prepared by well-known procedures. For example, the viral RNA is transcribed into DNA using reverse transcriptase to produce subgenomic DNA pieces, and a double-stranded DNA may be produced using DNA polymerases. The cDNA is then cloned into appropriate vectors and cloned into a cell to be transfected. In some instances, cDNA is first attached to a promoter which is compatible with the production cell. The recombinant plant viral nucleic acid can then be cloned into any suitable vector which is compatible with the production cell. Alternatively, the recombinant plant viral nucleic acid is inserted in a vector adjacent a promoter which is compatible with the production cell. In some embodiments, the cDNA ligated vector may be directly transcribed into infectious RNA in vitro and inoculated onto the plant host. The cDNA pieces are mapped and combined in proper sequence to produce a full-length DNA copy of the viral RNA genome, if necessary.

In some embodiments of the instant invention, increased representation of gene sequences in virus expression libraries may also be achieved by bypassing the genetic bottleneck of propagation in bacterial cells. For example, in some embodiments of the instant invention, cell-free methods may be used to assemble sequence libraries or individual arrayed sequences into virus expression vectors and reconstruct an infectious virus, such that the final ligation product can be transcribed and the resulting RNA can be used for plant, plant tissue or plant cell inoculation/infection. A more detailed discussion is presented in a co-pending and co-owned U.S. patent application No. 09/359,303 (Padgett et al., filed herewith, incorporated herein by reference).

Those skilled in the art will understand that these embodiments are representative only of many constructs suitable for housing libraries of sequence variants. All such constructs are contemplated and intended to be within the scope of the present invention. The invention is not intended to be limited to any particular viral constructs but specifically contemplates using all operable constructs. A person skilled in the art will be able to construct the plant viral nucleic acids based on molecular biology techniques well known in the art. Suitable techniques have been described in Sambrook et al. (2nd ed.), Cold Spring Harbor Laboratory, Cold Spring Harbor (1989); *Methods in Enzymol.* (Vols. 68, 100, 101, 118, and 152–155) (1979, 1983, 1986 and 1987); and *DNA Cloning*, D. M. Clover, Ed., IRL Press, Oxford (1985); Walkey, *Applied Plant Virology*, Chapman & Hall (1991); Matthews, *Plant Virology*, $3^{rd}$ Ed., Academic Press, San Diego (1991); Turpen et al., *J. of Virological Methods*, 42:227–240 (1993); U.S. Pat. Nos. 4,885,248, 5,173,410, 5,316,931, 5,466,788, 5,491,076, 5,500,360, 5,589,367, 5,602,242, 5,627,060, 5,811,653, 5,866,785, 5,889,190, and 5,589,367, U.S. patent application No. 08/324,003. Now U.S. Pat. No 5,977,348. Nucleic acid manipulations and enzyme treatments are carried out in accordance with manufacturers' recommended procedures in making such constructs.

II. Generating Libraries of Sequence Variants

One or more template sequences may be used to generate libraries of nucleic acid sequence variants via in vitro mutagenesis, recombination or a combination thereof. In some embodiments of the invention, the template sequences may be derived from viral elements. For example, if a plant virus is used as the genetic backbone for the recombinant viral nucleic acids, a nucleic acid sequence encoding elements (or parts thereof) such as the coat protein, movement protein, promoter sequences, internal initiation sites, packaging signals, 5' and 3' NTRs, or ribosomal sequences among others, may be selected as a template for generating a library containing variants of such nucleic acid sequence. The entire plant virus genomes may also be subjected to in vitro mutagenesis or recombination so to improve plant virus vector performance. In preferred embodiments, elements of the open reading frame (ORF) of RNA plant viruses is the starting point for sequence variation. Functions within the ORF include the movement protein (MP), the virus origin of virion assembly, the subgenomic promoter used for coat protein synthesis, among others.

In some embodiments of the invention, genes, regulatory sequences, or fragments thereof from prokaryotic and eukaryotic sources, such as bacteria, fungi, plants, animals, animal viruses, among others may serve as template sequences for generating sequence variants. For example, sequences regulating the transcription and translation of commercially useful proteins, polypeptides, or fusion products thereof, such as enzymes, antibodies, hormones, pharmaceuticals, vaccines, pigments, antimicrobial polypeptides, and the like may be used as templates to generate libraries of sequence variants.

The template nucleic acid sequence may be of various lengths. Preferably, the size of template nucleic acid sequence is from about 1 to 100,000 base pairs (bp), e.g. from about 2 to 50,000, from about 2 to 10,000, from about 2 to 5,000, from about 5 to 5,000, from about 10 to 2,000, etc. The number of sequence variants in a library may also vary depending on the method used. Typically, the number of sequence variants in a library is from about 2 to 100,000,000, e.g., from about 4 to 10,000,000, from about 16 to 1,000,000, from about 64 to 500,000, from about 64 to 100,000, from about 64 to 50,000, etc. In some instance, the number of sequence variants in a library may be unknown.

One skilled in the art will appreciate that there are many ways to generate sequence variants. A population of nucleic acid sequence variants may be found in nature. For example, a genomic library, a cDNA library, a pool of RNAs derived from bacteria, fungi, plants, or animals including humans, may be constructed. A more detailed discussion of generating such library is presented in a co-pending and co-owned U.S. patent application No. 09/359,300 (Kumagai et al., filed herewith, incorporated herein by reference). In some instances, natural sequence variations may consist of different alleles of the same gene or the same gene from different related species. Alternatively, they may be related nucleic acid sequences found within one species, for example, the immunoglobulin genes. In addition, the natural variations in plant and animal viral populations may also be the templates for generating sequence libraries.

In preferred embodiments, the sequence variants may be generated using in vitro mutagenesis methods, including, but not limited to, chemical treatment, oligonucleotide-mediated mutagenesis, PCR mutagenesis, and the like. The sequence variants may also be generated using in vitro recombination methods, including, but not limited to, DNA shuffling, random priming recombination (RPR), restriction enzyme fragment induced template switching (REFITS), and the staggered extension process (StEP), and other in vitro recombination methods. The sequence variants may also be generated using a combination of the methods mentioned above. The sequence populations may be random or selectively varied. Any source of nucleic acid can be utilized as the starting nucleic acid. Thus the process may employ DNA or RNA including messenger RNA, which DNA or RNA may be single or double stranded. In addition, a DNA-RNA hybrid which contains one strand of each may be utilized.

A. In vitro mutagenesis.

The nucleic acid sequence can be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. In some embodiments, these agents may be added to the PCR reaction in place of the nucleotide precursor thereby mutating the template sequence. Intercalating agents such as proflavine, acriflavine, quinacrine and the like can also be used. Random mutagenesis of the nucleic acid sequence can also be achieved by irradiation with X-rays or ultraviolet light.

In oligonucleotide-directed mutagenesis, a short synthetically mutagenized oligonucleotide incorporating the desired base changes is hybridized to the sequences to be altered (Sambrook, et al., *Molecular Cloning: A Laboratory Manual*, 2$^{nd}$ Ed. Cold Spring Harbor Laboratory Press, Cold Spring Harbor, N.Y., 1989 and Cleland et al., *Protein Engineering: Principles and Practice*, Wiley-Liss (1996)). The mismatched primer is then extended by polymerase, thereby generating the varied sequence. Individually varied sequences may be mixed and expressed together to select the desired function from such sequence mix. This approach is particularly useful in generating sequence variations that are close to each other.

Error-prone PCR may be employed to create libraries of point mutations (Eckert et al., *PCR Methods App.* 1:17–24 (1991); Caldwell et al., *PCR Methods App.* 2:28–33 (1992), Gramm et al., *Proc. Natl. Acad. Sci. USA* 89:3576–3580 (1992); and Cadwell et al., *PCR Methods App.* 3:S136–40 (1994); You et al. *Protein Eng.* 9:77–83 (1994)). This method uses a low fidelity replication to introduce random point mutations at each round of amplification. Repeated cycles of error-prone PCR may lead to accumulation of point mutations. Error prone PCR can be used to mutagenize a mixture of template sequences without knowing their nucleotide composition. Error-prone PCR is particularly suited when regions of mutagenesis are small, typically less than 1,000 base pairs.

Combinatorial cassette mutagenesis (Black et al., *Proc. Natl. Acad. Sci. USA* 93:3525–3529 (1996) and recursive ensemble mutagenesis (Delagrave et al., *Biotechnology* 11:1548–1552 (1993) and Arkin et al., *Proc. Natl Acad. Sci. USA* 89:7811–7815 (1992) may also be used to produce sequence variances. In cassette mutagenesis, a sequence block of a single template is typically replaced by a randomized or partially randomized sequence. Therefore, sequence variants are typically determined by the size of the sequence block and the number of random sequences. The randomized sequences may be derived from synthetically mutagenized oligonucleotides. Typically, the nucleotide compositions of the template sequences are known. In addition, cassette mutagenesis may employ *E. coli* strain XL1-red (Stratagene, Inc.). This *E. coli* strain has a high mutation rate from which a population of sequence variants may be derived.

B. In vitro recombination

1. DNA Shuffling

Nucleic acid shuffling is a method for in vitro homologous recombination of pools of nucleic acid sequence variants (U.S. Pat. Nos. 5,811,238, 5,605,793, 5,830,721, 5,834,252, and 5,837,458). This procedure involves random fragmentation of mixtures of related nucleic acid sequences followed by reassembly to yield a population of nucleic acid sequence variants.

The template polynucleotide may be DNA or RNA. It may be of various lengths depending on the size of the gene or nucleic acid fragment to be recombined or reassembled. Preferably the template polynucleotide is from 50 to 10,000 bp. The template polynucleotide should be double-stranded.

A double-stranded nucleic acid molecule is typically required to ensure that regions of the resulting single-stranded nucleic acid fragments are complementary to each other and thus can hybridize to form a double-stranded molecule. The template polynucleotide may be obtained by amplification using the PCR reaction. Free primers from the PCR products are typically removed before fragmentation to increase the frequency of crossover. Single-stranded or double-stranded nucleic acid fragments having regions of identity to the template polynucleotide and regions of heterology to the template polynucleotide may be added to the template polynucleotide. Different but related polynucleotide templates may be mixed. Double-stranded nucleic acids having multiple nicks may also be used.

The double-stranded polynucleotide template and any added double- or single-stranded fragments are randomly digested into fragments of from about 5 to 5,000 bp. Preferably the size of the random fragments is from about 10 to 1,000 bp, more preferably the size of the DNA fragments is from about 20 to 500 bp.

The nucleic acid fragment may be digested by a number of different methods. The nucleic acid fragment may be digested with a nuclease, such as Dnase I or Rnase. The nucleic acid may be randomly sheared by the method of sonication or by passage through a tube having a small orifice. The number of different specific nucleic acid fragments in the mixture may be at least about 100, preferably at least about 500, and more preferably at least about 1000. At this step single-stranded or double-stranded nucleic acid fragments, either synthetic or natural, may be added to the random double-stranded nucleic acid fragments in order to increase the heterogeneity of the mixture of nucleic acid fragments. Populations of double-stranded randomly broken nucleic acid fragments may be mixed or combined at this step.

Where insertion of mutations into the template polynucleotide is desired, single-stranded or double-stranded nucleic acid fragments having a region of identity to the template polynucleotide and a region of heterology to the template polynucleotide may be added in a 20 fold excess by weight as compared to the total nucleic acid, more preferably the single-stranded nucleic acid fragments may be added in a 10 fold excess by weight as compared to the total nucleic acid. Where a mixture of different but related template polynucleotides is desired, populations of nucleic acid fragments from each of the templates may be combined at a ratio of less than about 1:100, more preferably the ratio is less than about 1:40. For example, a backcross of the wild-type polynucleotide with a population of mutated polynucleotide may be desired to eliminate silent mutations. In such an example, the ratio of randomly digested wild-type polynucleotide fragments which may be added to the randomly digested mutant polynucleotide fragments is approximately 1:1 to about 100:1, and more preferably from 1:1 to 40:1.

The mixed population of random nucleic acid fragments are denatured to form single-stranded nucleic acid fragments and then reannealed. Only those single-stranded nucleic acid fragments having regions of homology with other single-stranded nucleic acid fragments will reanneal.

The random nucleic acid fragments may be denatured by heating. One skilled in the art could determine the conditions necessary to completely denature the double stranded nucleic acid. Preferably the temperature is from 80 ° C. to 100° C., more preferably the temperature is from 90° C. to 96° C. Other methods which may be used to denature the nucleic acid fragments include pressure and pH.

The nucleic acid fragments may be reannealed by cooling. Preferably the temperature is from 20° C. to 75° C., more preferably the temperature is from 40° C. to 65° C. If a high frequency of crossovers is needed based on an average of only 4 consecutive bases of homology, recombination can be forced by using a low annealing temperature. The degree of renaturation will depend on the degree of homology between the population of single-stranded nucleic acid fragments.

Renaturation can be accelerated by the addition of polyethylene glycol (PEG) or salt. The salt concentration is preferably from 0 mM to 200 mM, more preferably the salt concentration is from 10 mM to 100 mM. The salt may be KCl or NaCl. The concentration of PEG is preferably from 0% to 20%, more preferably from 5% to 10%.

The annealed nucleic acid fragments are next incubated in the presence of a nucleic acid polymerase and dNTP's (i.e. dATP, dCTP, dGTP and dTTP). The nucleic acid polymerase may be the Klenow fragment, the Taq polymerase, the Vent polymerase, or any other DNA polymerase known in the art.

The approach to be used for the assembly depends on the minimum degree of homology that should still yield crossovers. If the areas of identity are large, Taq polymerase can be used with an annealing temperature of between 45° C.–65° C. If the areas of identity are small, Klenow polymerase can be used with an annealing temperature of between 20° C.–30° C. One skilled in the art could vary the temperature of annealing to increase the number of crossovers achieved. The polymerase may be added to the random nucleic acid fragments prior to annealing, simultaneously with annealing or after annealing.

The cycle of denaturation, renaturation and incubation in the presence of polymerase is commonly referred to as shuffling or reassembly of the nucleic acid. This cycle is repeated for a desired number of times. Preferably the cycle is repeated from 2 to 50 times, more preferably the sequence is repeated from 10 to 40 times.

The resulting nucleic acid is a larger double-stranded polynucleotide of from about 50 to about 100,000 bp, preferably the larger polynucleotide is from 500 to 50,000 bp. This larger polynucleotide fragment may contain a number of copies of a nucleic acid fragment having the same size as the template polynucleotide in tandem. This concatemeric fragment is then digested into single copies of the template polynucleotide. The result will be a population of nucleic acid fragments of approximately the same size as the template polynucleotide. The population will be a mixed population where single or double-stranded nucleic acid fragments having an area of identity and an area of heterology have been added to the template polynucleotide prior to shuffling. The use of degenerate oligonucleotides in DNA shuffling to increase library diversity at specific sites may be useful under some circumstances.

The advantages of DNA shuffling are many: (1) sequences can be optimized without first determining the sites within the sequence that require alteration; (2) given proper selection, several generations of the improved sequences can be formed in a time frame unattainable by natural circumstances; and (3) mutations of every sort are randomly dispersed throughout the sequences, allowing a "saturation" approach to determine the genetic potential of a given sequence.

2. Random-priming Recombination (RPR)

Another simple and efficient method for in vitro recombination of nucleic acid sequences is random-priming recombination (RPR) (Shao et al., *Nucleic Acids Res.* 26:681–683 (1998)). In this method, random sequence primers are used to generate a large number of short DNA fragments complementary to different sections of the template sequences. Due to base misincorporation and mispriming, these short DNA fragments also contain a low level of point mutations. The short DNA fragments may prime one another based on homology, and be recombined and reassembled by repeated cycles of denaturation, annealing and further enzyme-catalyzed DNA polymerization to produce a library of full-length sequences. In particular, thermocycling in the presence of thermostable DNA polymerase may be used. Polymerases with different fidelities, including Klenow fragment of *E. coli* DNA polymerase I, bacteriophage T4 DNA polymerase, T7 Sequenase® DNA polymerase, the Stoffel fragment of Taq polymerase and Pfu polymerase, may be used for random priming DNA fragment synthesis. The length and concentration of random primer, as well as the time, temperature and other reaction conditions can also be manipulated by those skilled in the art in order to achieve the desired mutagenic rate and recombination frequency.

The RPR method offers several advantages. First, single-stranded polynucleotide templates without an intermediate step of synthesizing the second strand may be used in RPR. Potential mutations and/or crossovers may be introduced at the DNA level from single- or double-stranded DNA template by using DNA polymerases, or directly from mRNA by using RNA-dependent DNA polymerases. Second, DNA shuffling requires fragmentation of the double-stranded DNA template by nucleases, e.g. Dnase I. These nucleases need to be removed completely before the fragments can be reassembled into full length sequences. Sequence reassembly is generally easier with the RPR technique, which employs random priming synthesis to obtain the short DNA fragments. Furthermore, since Dnase I hydrolyzes double-stranded DNA preferentially at sites adjacent to pyrimidine nucleotides, its use in template digestion may introduce a sequence bias into the recombination. Third, the synthetic random primers are uniform in their length and lack sequence bias. The sequence heterogeneity allows them to form hybrids with the template DNA stands at many positions, so that, at least in principle, every nucleotide of the template should be copied or mutated at a similar frequency during extension. The random distribution of the short, nascent DNA fragments along the templates and the random distribution of point mutations within each nascent DNA fragment should guarantee the randomness of crossovers and mutations in the full length progeny genes. Fourth, the random-priming DNA synthesis is independent of the length of the DNA template. Fifth, since the template polynucleotide serves solely as the template for the synthesis of nascent, single-stranded DNA, 10–20 times less template DNA is needed as compared to DNA shuffling.

3. Restriction Enzyme Fragment Induced Template Switching (REFITS)

REFITS is a technically simple means of in vitro recombination between homologous DNA sequences. One of the technical challenges in DNA shuffling is reproducible generation of fragments of the appropriate size by Dnase. The Dnase I reaction is very sensitive to variations in template and enzyme concentrations. REFITS provides a different approach to generating fragments that is much easier to reproduce. It is a method to increase the rate of molecular evolution via in vitro homologous recombination of pools of mutant genes by fragmentation of the DNA with restriction enzymes and reassembly of fragments by PCR. The technique may be used to recombine homologous genes from related organisms, or to reassort random mutations, such as those generated by error-prone PCR.

The target DNA may be split into aliquots, and each aliquot is digested with a different restriction enzyme, or groups of restriction enzymes that cut the target DNA several times. Preferably, the restriction enzymes used in REFITS have four-base recognition site. In preferred embodiments, restriction enzymes are chosen to avoid large uncut fragments to improve the resolution of the recombination and help make sure that no large region remains unshuffled. The resolution of the recombination is determined by how close two mutations can be and still be separated and recombined at a detectable level. The resolution is also increased by using more enzymes to generate more pools of fragments. Since each separate digestion is done to completion, no careful timing of digestion is required, unlike Dnase I partial digestion. Some partial digestion products may also be tolerated by the REFITS procedure.

4. Staggered Extension Process (StEP)

Staggered extension process (StEP) is another simple and efficient method for in vitro recombination of polynucleotide sequences to generate libraries of sequence variants (Zhao et al., *Nat. Biotechnol.* 16:258–261 (1998)). Rather than reassembling recombined sequences from a pool of fragmented template sequences, StEP prepares full-length recombined genes in the presence of the templates. Essentially, StEP consists of priming the template sequences followed by repeated cycles of denaturation and extremely abbreviated annealing/polymerase-catalyzed extension. This limited polymerase extension time is used to generate less-than-full-length fragments. In each cycle the growing fragments anneal to different templates based on sequence complementarity and extend further to create "recombination cassettes." This is repeated until full-length sequence form. Due to template switching, most of the polynucleotides contain sequence information from different template sequences. The speed of the thermal cycle may be adjusted to avoid the polymerase adding too many bases at each cycle. Adding too many bases at each cycle may limit the amount of possible template switches and so limiting the amount of recombination and resolution between template switches. StEP may be performed using flanking universal primers to avoid bias introduced from the starting primers.

StEP recombination reaction may be carried out in a single tube and separation of template templates from the recombined products may not be necessary. StEP may be followed by a gene amplification step, if desired.

It is further contemplated that various methods of in vitro mutagenesis and recombination may be combined to generate sequence libraries. It is also contemplated that a number of cycles of in vitro mutagenesis and recombination may be conducted with nucleic acid fragments from a subpopulation of the first population, which subpopulation contains desired nucleic acids. It is also contemplated that a number of cycles of in vitro mutagenesis and recombination may be conducted with a mixture of template nucleic acid fragments and a subpopulation of nucleic acid from the first or subsequent rounds.

III. Expressing Libraries of Nucleic Acid Sequence Variants in Plant Hosts

Once the population of the nucleic acid sequence variants is generated, the polynucleotides can be used directly, amplified using PCR based-technologies, or inserted into an appropriate cloning vector, using techniques well-known in the art. Libraries may often be first constructed in plasmid or phage shuttle vectors before excising and introducing into virus vectors. Likewise, sequences can be screened in hosts using virus vectors, but must be subcloned into appropriate eukaryotic expression vectors before the trait identified in the vector transfected host will become a stable trait in the host by gene integration. The choice of vector depends on the size of the polynucleotide sequence and the plant host to be employed in the methods of this invention. Suitable restriction sites to facilitate the insertion of sequence variants into viral vectors may be added.

Viral nucleic acids containing a population of sequence variants can be transfected as populations or individual clones into host: 1) protoplasts; 2) whole plants; or 3) plant tissues, such as leaves of plants (Dijkstra et al., *Practical Plant Virology: Protocols and Exercises,* Springer Verlag (1998); *Plant Virology Protocol: From Virus Isolation to Transgenic Resistance* in *Methods in Molecular Biology,* Vol. 81, Foster and Taylor, Ed., Humana Press (1998)). The plant host may be a monocotyledonous or dicotyledonous plant, plant tissue, or plant cell. Typically, plants of commercial interest, such as food crops, seed crops, oil crops, ornamental crops and forestry crops are preferred. For example, wheat, rice, corn, potato, barley, tobacco, soybean canola, maize, oilseed rape, lilies, grasses, orchids, irises, onions, palms, tomato, the legumes, or Arabidopsis, can be used as a plant host. Host plants may also include those readily infected by an infectious virus, such as Nicotiana, preferably, *Nicotiana benthamiana,* or *Nicotiana clevelandii.*

In some embodiments of the instant invention, the delivery of the plant virus expression vectors into the plant may be affected by the inoculation of in vitro transcribed RNA, inoculation of virions, or internal inoculation of plant cells from nuclear cDNA, or the systemic infection resulting from any of these procedures. In all cases, the co-infection may lead to a rapid and pervasive systemic expression of the desired nucleic acid sequences in plant cells. The systemic infection of the plant by the foreign sequences may be followed by the growth of the infected host to produce the desired product, and the isolation and purification of the desired product, if necessary. The growth of the infected host is in accordance with conventional techniques, as is the isolation and the purification of the resultant products.

The host can be infected with a recombinant viral nucleic acid or a recombinant plant virus by conventional techniques. Suitable techniques include, but are not limited to, leaf abrasion, abrasion in solution, high velocity water spray, and other injury of a host as well as imbibing host seeds with water containing the recombinant viral RNA or recombinant plant virus. More specifically, suitable techniques include:

(a) Hand Inoculations. Hand inoculations are performed using a neutral pH, low molarity phosphate buffer, with the addition of celite or carborundum (usually about 1%). One to four drops of the preparation is put onto the upper surface of a leaf and gently rubbed.

(b) Mechanized Inoculations of Plant Beds. Plant bed inoculations are performed by spraying (gas-propelled) the vector solution into a tractor-driven mower while cutting the leaves. Alternatively, the plant bed is mowed and the vector solution sprayed immediately onto the cut leaves.

(c) High Pressure Spray of Single Leaves. Single plant inoculations can also be performed by spraying the leaves with a narrow, directed spray (50 psi, 6–12 inches from the leaf) containing approximately 1% carborundum in the buffered vector solution.

(d) Vacuum Infiltration. Inoculations may be accomplished by subjecting a host organism to a substantially vacuum pressure environment in order to facilitate infection.

(e) High Speed Robotics Inoculation. Especially applicable when the organism is a plant, individual organisms may be grown in mass array such as in microtiter plates. Machinery such as robotics may then be used to transfer the nucleic acid of interest.

(f) Ballistics (High Pressure Gun) Inoculation. Single plant inoculations can also be performed by particle bombardment. A ballistics particle delivery system (BioRad Laboratories, Hercules, (A) can be used to transfect plants such as *N. benthamiana* as described previously (Nagar et al., *Plant Cell,* 7:705–719 (1995)).

An alternative method for introducing viral nucleic acids into a plant host is a technique known as agroinfection or Agrobacterium-mediated transformation (also known as Agro-infection) as described by Grimsley et al., *Nature* 325:177 (1987). This technique makes use of a common feature of Agrobacterium which colonizes plants by transferring a portion of their DNA (the T-DNA) into a host cell, where it becomes integrated into nuclear DNA. The T-DNA is defined by border sequences which are 25 base pairs long, and any DNA between these border sequences is transferred to the plant cells as well. The insertion of a recombinant plant viral nucleic acid between the T-DNA border sequences results in transfer of the recombinant plant viral nucleic acid to the plant cells, where the recombinant plant viral nucleic acid is replicated, and then spreads systemically through the plant. Agro-infection has been accomplished with potato spindle tuber viroid (PSTV) (Gardner et al., *Plant Mol. Biol.* 6:221 (1986); CaV (Grimsley et al., *Proc. Natl. Acad. Sci. USA* 83:3282 (1986)); MSV (Grimsley et al., *Nature* 325:177 (1987)), and Lazarowitz, S., *Nucl. Acids Res.* 16:229 (1988)) digitaria streak virus (Donson et al., *Virology* 162:248 (1988)), wheat dwarf virus (Hayes et al, *J. Gen. Virol.* 69:891 (1988)) and tomato golden mosaic virus (TGMV) (Elmer et al., *Plant Mol. Biol.* 10:225 (1988) and Gardiner et al., *EMBO J.* 7:899 (1988)). Therefore, agro-infection of a susceptible plant could be accomplished with a virion containing a recombinant plant viral nucleic acid based on the nucleotide sequence of any of the above viruses. Particle bombardment or electrosporation or any other methods known in the art may also be used.

In some embodiments of the instant invention, infection may also be attained by placing a selected nucleic acid sequence into an organism such as *E. coli,* or yeast, either integrated into the genome of such organism or not, and then applying the organism to the surface of the host organism. Such a mechanism may thereby produce secondary transfer of the selected nucleic acid sequence into a host organism. This is a particularly practical embodiment when the host organism is a plant. Likewise, infection may be attained by first packaging a selected nucleic acid sequence in a pseudovirus. Such a method is described in WO 94/10329. Though the teachings of this reference may be specific for bacteria, those of skill in the art will readily appreciate that the same procedures could easily be adapted to other organisms.

IV. Screening and Selecting Desired Traits

After a plant host is infected with a population of sequence variants or individual clone of the population, one or more desired traits are screened and selected. The desired traits may include biochemical or phenotypic traits. Phenotypic traits may include, but not limited to, host range, viral infectivity, tolerance to herbicides, tolerance to extremes of heat or cold, drought, salinity or osmotic stress; resistance to pests (insects, nematodes or arachnids) or diseases (fungal, bacterial or viral), male or female sterility, dwarfness, early maturity; improved yield, vigor, heterosis, nutritional qualities, flavor or processing properties, and the like. Biochemical traits may be related to, for example, promoter activities, replication activities, translational activities, regulatory activities, movement activities (local and systemic), signaling activities, extraction/purification properties, etc. It should be noted that many biochemical traits also exhibit phenotypic traits and vice versa. The screening of sequence libraries is typically followed by rescue of the viruses from populations conferring desired traits. If necessary, re-screening of sub-libraries may be performed. In some embodiments, sequences of the viral nucleic acids conferring desired traits may be determined and compared with the template sequences.

To screen the desired traits, biochemical or phenotypic changes in a host plant is determined. The biochemical or phenotypic changes in the infected host plant may be correlated to the biochemistry or phenotype of a host plant that is uninfected. Optionally, the biochemical or phenotypic changes in the infected host plant is further correlated to a host plant that is infected with a viral vector that contains a control nucleic acid of a known sequence. The phenotypic changes in a plant host may be determined by any known methods in the art. Typically, these methods include visual, morphological, macroscopic or microscopic analysis. For example, growth changes, such as stunting, color changes (e.g. leaf yellowing, mottling, bleaching, chlorosis) among others are easily visualized. Examples of morphological changes include, developmental defects, wilting, necrosis, among others. Biochemical changes can be determined by any analytical methods known in the art for detecting, quantitating, or isolating DNA, RNA, proteins, antibodies, carbohydrates, lipids, and small molecules. Selected methods may include Northern, Western blotting, MALDI-TOF, LC/MS, GC/MS, two-dimensional IEF/SDS-PAGE, ELISA, etc. In particular, suitable methods may be performed in a high-throughput, fully automated fashion using robotics. Examples of biochemical changes may include the accumulation of substrates or products from enzymatic reactions, changes in biochemical pathways, inhibition or augmentation of endogenous gene expression in the cytoplasm of cells, changes in the RNA or protein profile.

Those of skill in the art will readily understand that there are many methods to determine phenotypic or biochemical changes in a plant host and to select one or more viral nucleic acids that confer the selected traits. In some embodiments, infected plant hosts capable of growing or maintaining viability in the presence of noxious or toxic substances, such as herbicides and pharmaceutical ingredients, may be selected.

Host plants vary in their ability to support expression of recombinant viral nucleic acids. Some species support expression to a high specific activity (such as *Nicotiana benthamiana*) but have relatively low biomass. Other species (such as *N. tabacum*) have high biomass and/or other desirable properties for growth in the field, but have a relatively low specific activity of the expressed sequence. In some embodiments, the plant hosts capable of producing optimal level of non-native products, such as enzymes, antibodies, hormones, pharmaceuticals, vaccines, pigments, antimicrobial polypeptides, and the like may be selected.

In some embodiments, inhibition of proteolytic activity in plants which is responsible for the degradation of recombinant proteins is often desired. Selection of inhibition of proteolytic activity in plants may use a library of viral sequence variants. The size and yield of protein of interest are determined and the desired results are correlated with members of the viral sequence variants.

The functions of transcription factors contributing to the signal transduction pathway of host cells can be monitored by using specific proteomic, mRNA or metanomic traits to be assayed following transfection with a virus expression library. The contribution of a particular protein or product to a valuable trait may be known from the literature, but a new mode of enhanced or reduced expression could be identified by finding the factors that alter its particular expression. For example, transcription factors regulating the expression of defense proteins such as systemin peptides, or protease inhibitors could be identified by transfecting hosts with virus libraries and the expression of systemin or protease inhibitors or their RNAs be directly assayed. Conversely, the promoters responsible for expressing these genes could be genetically fused to the green fluorescent protein and introduced into hosts as transient expression constructs or into stable transformed host cells/tissues. The resulting cells would be transfected with viral vector libraries. Those members of the library which altered the activity of the promoter of interest fused to the GFP reporter gene could be readily identified by monitoring changes of GFP expression (either an increase or a decrease in expression) in infected plant tissues, such as leaves.

In some embodiments, a DNA fragment which encodes for a protein with increased binding efficiency to a ligand is desired. The proteins expressed by each nucleic acid in the library may be tested for their ability to bind to the ligand by methods known in the art (i.e. panning, affinity chromatography). If a nucleic acid which encodes for a protein with increased drug resistance is desired, the proteins expressed by each of the nucleic acid in the population or library may be tested for their ability to confer drug resistance to the host organism.

For treatment of hosts with agents that result in cell death or down regulation in general metabolic function, a virus vector, which simultaneously express the green fluorescent protein (GFP) or other selectable marker gene and the variant sequence, is used to screen quantitatively for levels of resistance or sensitivity to the agent in question conferred upon the host by the variant sequence expressed from the viral vector. By quantitatively screening pools or individual infection events, those viruses containing unique variant sequences allowing sustained metabolic life of host are identified by fluorescence under long wave UV light. Those that do not confer this phenotype will fail to or poorly fluoresce. In this manner, high throughput screening in multi-well dishes in plate readers is possible where the average fluorescence of the well would be expressed as a ratio of the adsorption (measuring the cell mass) thereby giving a comparable quantitative value.

Recombinant proteins expressed in cells often do not have the desired solubility and processing/purification characteristics, making their purification tedious or problematic. One may alter amino acid sequence of a protein or protein-fusion of interest so that the resulting modified protein has desired characteristics of solubility, stability, etc. In some embodiments of the invention, a carrier protein-protein fusion of interest may be constructed to identify specific variants with altered purification properties. A reporter protein, such as, but not limited to proteins such as GFP or antibiotic/herbicide resistance genes, etc. can be used as potential carrier proteins for polypeptides of interest. The variants can be screened by detecting either the polypeptide of interest (using an appropriate assay) or by assaying for the carrier protein. For example, if a GFP-peptide fusion is expressed in plant hosts by observing GFP activity under long wave UV. In this way carrier protein-protein fusions with altered solubility and/or stabilities may be screened for. This approach can also be used to examine the purification properties of carrier protein-protein variants. For example, protein samples can be prepared from cells expressing different variants of a carrier-protein-protein fusion (these extracts can be from extracellular, secreted, protein or intracellular proteins). These extracts can be run through a series of different partial purification steps such as (but not limited to) treatments of various pHs and temperatures, centrifugation steps, etc. Finally the treated samples can be assayed for the presence of either the carrier protein domain of the fusion of the protein of interest, for example, in order to estimate the amount of protein that survives the purification regimes. Variants with characteristics of interest can be isolated for more experimentation and or modification if desired.

Other selectable traits may include: 1) selection of viruses or viral vectors with altered host range, tissue tropisms, and cell-to-cell or systemic movement properties; 2) selection of virus cis-acting or trans-acting sequences or encoded products which alter regulation (transcription or message stability) of native or foreign gene expression in viruses or viral vectors; 3) selection of sequences that flank foreign sequence additions that alter translation of foreign sequences; 4) selection of sequences that flank foreign sequence additions that increase the genetic stability of specific or general foreign sequences ligated into virus vectors; 5) incorporation of flanking sequences or sequences internal to a sequence motif to be expressed that mediate appropriate conformational presentation of epitopes that are fused to native or modified virus proteins or other carrier proteins; 6) selection of sequences that can replace structural elements in native or modified virus proteins; 7) selection of sequences that can be added and structurally tolerated to native or modified virus proteins which add functionality to the encoded protein; 8) incorporation of down-regulating mutations into virus encoded cis- or trans-acting virus sequences and the selection of variants, induced or naturally occurring, that are second-site revertants, thereby restoring part of the whole of the impaired functionality; 9) selection of sequences added into foreign or native/modified virus proteins which promote the proper folding, sub-cellular localization, expression levels, extraction/purification properties, and activity of protein of the interest; and 10) incorporation of sequences that remove non-viral RNA sequences from in vitro derived transcripts of virus or viral vectors, which include, but are not limited to, ribozymes.

In order to provide a clear and consistent understanding of the specification and the claims, including the scope given herein to such terms, the following definitions are given:

5' or 3' NTR: nontranslated region of a viral genome at the 5' or 3' end.

Cis-acting (cis-dependent): interaction of a molecule or complex with itself or between a gene product with the nucleic acid from which it was expressed.

Coat protein (capsid protein): an outer structural protein of a virus.

Gene: a discrete nucleic acid sequence responsible for a discrete cellular product.

Host: a cell, tissue or organism capable of replicating a vector or viral nucleic acid and which is capable of being infected by a virus containing the viral vector or viral nucleic acid. This term is intended to include prokaryotic and eukaryotic cells, organs, tissues, organisms, or in vitro extracts thereof, where appropriate.

Infection: the ability of a virus to transfer its nucleic acid to a host or introduce viral nucleic acid into a host, wherein the viral nucleic acid is replicated, viral proteins are synthesized, and new viral particles assembled.

Internal initiation site: any of the internal regions that direct ribosome-mediated translation of mRNA into polypeptides.

Movement protein: a noncapsid protein required for cell-to-cell movement of RNA replicons or viruses in plants.

Non-native (foreign): any sequence that does not normally occur in the virus or its host.

Open Reading Frame: a nucleotide sequence of suitable length in which there are no stop codons.

Packaging signal: the RNA sequence(s) responsible for enclosing the RNA within the capsid or coat protein(s) to form a mature virion.

PCR: a broad range of polynucleotide amplification techniques for increasing the number of copies of specific polynucleotide sequences. Examples of polynucleotide amplification reactions include, but not limited to, polymerase chain reaction (PCR, U.S. Pat. Nos. 4,683,202 and 4,683,195), reverse transcriptase PCR (RT-PCR), nucleic acid sequence based amplification (NASB), self-sustained sequence replication (3SR), strand displacement activation (SDA), ligase chain reaction (LCR), rolling-circle amplification (RCA), Qβ replicase system, and the like (Isaksson and Landegren, *Curr. Opin. Biotechnol.* 10:11–15 (1999); Landegren, *Curr. Opin. Biotechnol.* 7:95–97 (1996); and Abramson et al., *Curr. Opin. Biotechnol.* 4:41–47 (1993)).

Plant Cell: the structural and physiological unit of plants, consisting of a protoplast and the cell wall.

Plant Tissue: any tissue of a plant in planta or in culture. This term is intended to include a whole plant, plant cell, plant organ, protoplast, cell culture, or any group of plant cells organized into a structural and functional unit.

Promoter: the 5'-flanking, non-coding sequence adjacent to a coding sequence which is involved in the initiation of transcription of the coding sequence.

Protoplast: an isolated cell without cell walls, having the potency for regeneration into cell culture or a whole host.

Subgenomic mRNA promoter: a promoter that directs the synthesis of an mRNA smaller than the full-length genome in size.

Trans-acting: interaction of a molecule or complex on other molecule(s) independent from itself or independent from the nucleic acid from which it was expressed.

Vector: a self-replicating nucleic acid molecule that contains non-native sequences and which transfers nucleic acid segments between cells.

Virion: a particle composed of viral nucleic acid, viral coat protein (or capsid protein).

Virus: an infectious agent composed of a nucleic acid encapsulated in a protein.

EXAMPLES OF THE PREFERRED EMBODIMENTS

The following examples further illustrate the present invention. These examples are intended merely to be illustrative of the present invention and are not to be construed as being limiting.

Example 1

Tobacco mosaic virus (TMV) is a positive-stranded ssRNA virus whose genome is 6395 nucleotides long. The genomic RNA contains a short 5' NTR followed by an open reading frame (ORF) of 4848 nucleotides, which includes an amber stop codon at nucleotide 3417. Two non-structural proteins are expressed from this ORF. The first is a 126 kDa protein containing the nucleotide binding and putative helicase activities. The second is a 183 kDa protein, which is a translational read through of the amber stop codon in about 5–10% of the translational events. The 183 kDa protein contains the functional domains of the 126 kDa protein and a novel domain with homology to RNA-dependent RNA polymerases. At least two subgenomic mRNAs with a common 3' terminus are also produced after TMV infection. These encode a 30 kDa movement protein and a 17.5 kDa coat protein. The 3' terminus of TMV genomic RNA can be folded into a series of pseudoknots followed by a tRNA-like structure.

The coding region for the 30 kDa movement protein from TMV U1 for movement properties in *Nicotiana tabacum* and subgenomic promoter activity responsible for coat protein mRNA production were modified to generate populations of sequence variants. The base expression vector, p30B GFP, was used as a tool to be modified as desired for a shuffling vector. p30B GFP vector is the TMV U1 infectious cDNA (bases 1–5756) containing the 5' NTR, replicase genes (126 and 183 kDa proteins), movement protein gene with associated subgenomic promoter and an RNA leader derived from the U1 coat protein gene. Following the RNA leader is a unique PacI site and the green fluorescent protein (GFP) gene. Following a unique XhoI site, the clone continues with a portion of the TMV U1 3' NTR followed by a subgenomic promoter, coat protein gene and 3' NTR from TMV U5 strain.

The first stage of this experiment is the construction of a vector into which shuffled DNA fragments may be reintroduced. The polymerase chain reaction (PCR) was used to amplify a DNA fragment from the TMV vector p30B comprising the T7 promoter, 5' NTR, and the reading frames for the 126 and 183 kDa replicase proteins. The 5' primer covered the T7 promoter and initial bases of the TMV genome while the second primer modified the context surrounding the start codon for the 30 kDa MP of TMV. This allowed DNA fragments to be ligated into the modified vector, designated 30B GFP d30K, as AvrII, PacI restriction endonuclease digested fragments.

```
Native TMV 183/30 kDa junction and 30k/GFP junction
183 kDa ORF
AGT TTG TTT ATA GAT GGC TCT AGT TGT TAA AGG AAA A...GAT TCG TTT TAA (cont.)
 S   L   F   I   D   G   S   S   C   *   (SEQ ID NO:2)
                         M   A   L   V   K   G   K... D   S   F   *  (SEQ ID NO:3)
                        30kDa ORF
```

-continued

```
ATAgaTCTTACAGTATCACTACTCCATCTCAGTTCGTGTTCTTGTCATTAATTAA ATG...   (SEQ ID NO:1)
                                                  PacI     GFP ORF

Modified TMV 183/30 kDa/GFP junction (without 30 kDa gene): p30B d30k ANP
183 kDaORF
AGT TTG TTT ATA GAc GGC TCT AGT TGT TAA g CCTAGGAGCCGGCTTAATTAA ATG...(SEQ ID NO:4)
GFP ORF
S   L   F   I   D   G   S   S   C   *    AvrII        NgoMI
 PacI   (SEQ ID NO:5)

Modified TMV 183/30 kDa junction and 30k/GFPjunction (with 30 kDa gene
present)
183 kDa ORF
AGT TTG TTT ATA GAT GGC TCT AGT TGT TAA g ATG GCT CTA GTT GTT AAA GGA
AAA.(cont.)
S   L   F   I   D   G   S   S   C   *     AvrII (SEQ ID NO:7)
                                           M   A   L   V   V   K   G   K...(SEQ ID NO:8)

..GTTTTAAATAgaTCTTACAGTATCACTACTCCATCTCAGTTCGTGTTCTTGTCATTAATTAA ATG...(SEQ ID NO:6)
                                                          PacI     GFP ORF
```

This modification allowed the ready insertion of modified 30 kDa gene fragments into a virus vector and have them expressed in plant cells, tissues or systemically. The wild type GFP ORF is the reporter gene since the visual level of fluorescence as observed under long wave UV light correlates directly with levels of GFP protein present in plant tissues. This has been demonstrated by looking at different virus vectors expressing GFP, each having different strength subgenomic promoters, that were infected in plants and GFP levels determined by UV fluorescence and Western blotting using anti-GFP antibodies.

The procedure for shuffling of the 30 kDa gene is similar to that described by Crameri et al, *Nat. Biotechnol.* 15:436–438 (1997), and contained the following steps. The 30 kDa gene fragment also containing the coat protein RNA leader was amplified from tobamovirus expression vectors using primers: TMVU1 30K 5'A (5'-GGCCCTAGGATGGCTCTAGTTGTTAAAGG-3') (SEQ ID NO: 9) and 3-5' Pac primer (5'-GTTCTTCTCCTTTGCTAGCCATTTAATTAATGAC-3') (SEQ ID NO: 10). The PCR DNA product was gel isolated and then incompletely digested with DNaseI. DNA fragments of 500 bp or smaller were isolated by using DEAE blotting paper technique and then eluted. Purified DNA fragments were mixed together with taq DNA polymerase and allowed to "reassemble" for 40 cycles. "Reassembly" reaction was assayed by gel electrophoresis for DNA bands of approximately 800–850 bp. Approximately 1 mcl of the "reassembly" reaction was then subjected to PCR using primers TMV U1 30K 5+A and 3-5' Pac that hybridize to terminal DNA ends of reassembled fragments. The reassembled fragments will be gel isolated and digested with restriction enzymes AvrII and PacI (sites present in the terminal primers) to allow for facile cloning back into the p30B d30k ANP digested with AvrII and PacI.

Ligations of shuffled genes into p30B d30k ANP resulted in pooled libraries of sequences containing 100 to 50,000 members in five separate experiments. Pooled virus vectors with libraries of variant 30 kDa coding regions were transcribed with T7 RNA polymerase and then inoculated by standard PEG mediated transfection into $0.5\times10^6$ *Nicotiana tabacum* protoplasts per sample. Inspection of cells 24 hours post inoculation revealed varied intensities of GFP fluorescence in individual cells indicating possible different levels of GFP accumulation and possible effects in the subgenomic promoter activity as desired. Cells were incubated for 48 hours post inoculation, harvested by centrifugation and then lysed using freeze/thaw and grinding with a mortar and pestle. The virions that accumulated in protoplasts were released by the grinding.

The protoplast extracts were then inoculated on leaves of wild type and transgenic *Nicotiana tabacum* c.v. MD609 expressing the TMV U1 30 kDa movement protein. Three to five days post inoculation localized infection sites were observed expressing GFP. A variety of intensities of GFP fluorescence were observed varying from that observed with the wild type GFP gene to much duller to very bright. The occurrence of viruses expressing enhanced GFP fluorescence varied between libraries tested from 1/200 to 1/50 infection foci depending on libraries tested. These local infection sites with enhanced GFP fluorescence were excised from the leaves and inoculated on *Nicotiana benthamiana* plants. The bright local infection variants were then purified on the inoculated leaves of these plants from contaminating viruses expressing less GFP protein. These viruses expressing brighter GFP proteins were found to express larger amounts of GFP protein in systemic tissues than the starting p30B GFP virus. Sequencing and genetic studies indicated that no mutations accumulated in the GFP genes and that the effects were due to mutations in the TMV U1 30 kDa ORF that up regulated the subgenomic promoter. The accumulation of GFP in the shuffled variants with brighter GFP phenotype was 3.4 fold greater than that produced by p30B GFP as measured by quantitative Western blotting of plant extracts using an anti-GFP sera. These data demonstrated that shuffling could be used to enhance the cis-acting functions of RNA sequences and that plant RNA virus expression vectors are effective tools to shuttle large diversity of sequence variants in whole plants and plant cells.

The protoplast extracts isolated from transfections with virus libraries were inoculated on one half of wild type *Nicotiana tabacum* c.v. MD609 and *Nicotiana benthamiana* leaves. To the other leaf half, virus derived from p30B GFP was inoculated. Some infection sites resulting from infection of viruses containing shuffled 30 kDa ORFs grew more rapidly than those of the average from p30B GFP. These events occurred at a frequency of 1/100 to 1/500 infection foci depending on the virus library analyzed. These more rapidly growing infection foci were excised and inoculated on young *Nicotiana tabacum* c.v. MD609 plants. As a control, p30B GFP was inoculated on similar sized and aged plants. Some shuffled 30 kDa ORF variant vectors, that were identified as rapidly growing local infection sites, were able to move systemically on tobacco plants at a faster rate than the control virus. This movement ability was reproducible in multiple inoculations of these individual virus variants. Sequence analysis of the viruses containing shuffled 30 kDa ORFs capable of systemic movement on Nicotiana tabacum plants demonstrated that localized amino acid substitutions were present.

Further recursive shuffling of the top 5–10% of GFP expressing vectors or those that demonstrated an enhanced ability to invade systemic tissues of tobacco could be carried out to meld synergistic mutations to lead to greater gains in expression or virus movement. Likewise, the 30 kDa ORFs that contain the most potent subgenomic promoters and most enabled movement activities in tobacco could be shuffled together so to bring both sets of properties into the same 30 kDa ORF. It is also apparent from these data that by testing virus expression vectors containing libraries of these shuffled variants, one can select the variant with the protein or RNA activity that one desires. The phenotypes that can be assayed are protein activity in planta, as with the movement activities of the 30 kDa protein, enzyme activities in planta or in plant extracts or other surrogate features such as substrate or product accumulation. These data demonstrate the power of virus expression vectors to be effective tools for shuttling sequence variants into plants and allow the selection of genes encoding the desired altered property. This tool allows one to mine the hidden activities, enhance the isolated activities of enzymes or eliminate allosteric inhibition of enzyme activities. This could be applied to any plant gene or genes from other sources to optimize the activities desired for agronomic, pharmaceutical or developmental effects caused by altered genes.

Example 2
Novel Requirements for Production of Infectious Viral Vector in vitro Derived RNA Transcripts This example demonstrates the selection of highly infectious viral vector transcripts by introducing extra random nucleotides at the 5' end of viral vectors.

Construction of a library of subgenomic cDNA clones of TMV and BMV has been described in Dawson et al., *Proc. Natl. Acad. Sci. USA* 83:1832–1836 (1986) and Ahlquist et al., *Proc. Natl. Acad. Sci. USA* 81:7066–7070 (1984). Nucleotides were added between the transcriptional start site of the promoter for in vitro transcription, in this case T7, and the start of the cDNA of TMV in order to examine the effect of 5' non viral encoded nucleotides on transcript infectivity. The relevant sequence is the T7 promoter . . . TATA-G^ATATTTT . . . (SEQ ID NO:11) where the ^ indicates the base preceding is the start site for transcription and the bold letter is the first base of the TMV cDNA. Three approaches were taken: 1) addition of G, GG or GGG between the start site of transcription and the TMV cDNA ( . . . TATAGG-TATTT . . . and associated sequences) (SEQ ID NO:12); 2) addition of G and a random base (GN or N2) or a G and two random bases (GNN or N3) between the start site of transcription and the TMV cDNA ( . . . TATAGNTATTT . . . and associated sequences) (SEQ ID NO:13), and the addition of a GT and a single random base between the start site of transcription and the TMV cDNA ( . . . TATAGTNG TATTT . . . (SEQ ID NO:14) and associated sequences). Approaches included cloning GFP expressing TMV vector sequences into vectors containing extra G, GG or GGG bases using standard molecular biology techniques. Likewise, full length PCR of TMV expression clone 1056 was done to add N2, N3 and GTN bases between the T7 promoter and the TMV cDNA. Subsequently, these PCR products were cloned into pUC based vectors. Capped and uncapped transcripts were made in vitro and inoculated to tobacco protoplasts or *Nicotiana benthamiana* plants, wild type and 30 k expressing transgenics. The results are that an extra G, . . . TATAGGTATTTT . . . (SEQ ID NO:15), or a GTC, . . . TATAGTCGTATTTT . . . (SEQ ID NO:16), were found to be well tolerated as additional 5' nucleotides on the 5' of TMV vector RNA transcripts and were quite infectious on both plant types and protoplasts as capped or non-capped transcripts. Other sequences may be screened to find other options. Clearly, infectious transcripts may be derived with extra 5' nucleotides.

Other derivatives based on the mechanistic function of the GTN strategy that yielded the GTC functional vector are to use multiple GTN motifs preceding the 5' most nucleotides of the virus cDNA or the duplication of larger regions of the 5'-end of the TMV genome. For example: TATA^GTNGT-NGTATT . . . (SEQ ID NO:17) or TATA^GTNGTNGTNGT-NGTATT . . . (SEQ ID NO:18), or TATA^GTATTTGT ATTT . . . (SEQ ID NO:19) This strategy can be applied to a range of RNA viruses or RNA viral vectors of various genetic arrangements derived from wild type virus genome. This would require the use of sequences particular to that of the virus used as a vector.

Example 3
Infectivity of Uncapped Transcripts.

Two TMV-based virus expression vectors were initially used in these studies pBTI 1056 which contains the T7 promoter followed directly by the virus cDNA sequence ( . . . TATAGTATT . . . ), and pBTI SBS60-29 which contains the T7 promoter (underlined) followed by an extra guanine residue then the virus cDNA sequence ( . . . TATAGGT ATT . . .)(SEQ ID NO:20). Both expression vectors express the cycle 3 shuffled green fluorescent protein (GFPc3) in localized infection sites and systemically infected tissue of infected plants. Transcriptions of each plasmid were carried out in the absence of cap analogue (uncapped) or in the presence of 8-fold greater concentration of RNA cap analogue than rGTP (capped). Transcriptions were mixed with abrasive and inoculated on expanded older leaves of a wild type *Nicotiana benthamiana* (Nb) plant and a Nb plant expressing a TMV U1 30k movement protein transgene (Nb 30 K). Four days post inoculation (dpi) long wave UV light was used to judge the number of infection sites on the inoculated leaves of the plants. Systemic, noninoculated tissues, were monitored from 4 dpi on for appearance of systemic infection indicating vascular movement of the inoculated virus. Table 1 shows data from one representative experiment.

TABLE 1

| Construct | Local infection sites | | Systemic Infection | |
| --- | --- | --- | --- | --- |
| | Nb | Nb 30K | Nb | Nb 30K |
| pBTI1056 | | | | |
| Capped | 5 | 6 | yes | yes |
| Uncapped | 0 | 5 | no | yes |
| PBTI SBS60-29 | | | | |
| Capped | 6 | 6 | yes | yes |
| Uncapped | 1 | 5 | yes | yes |

*Nicotiana tabacum* protoplasts were infected with either capped or uncapped transcriptions (as described above) of pBTI SBS60 which contains the T7 promoter followed directly by the virus cDNA sequence (TATAGTATT . . . ).

This expression vector also expresses the GFPc3 gene in infected cells and tissues. *Nicotiana tabacum* protoplasts were transfected with 1 mcl of each transcriptions. Approximately 36 hours post infection transfected protoplasts were viewed under UV illumination and cells showing GFPc3 expression. Approximately 80% cells transfected with the capped PBTI SBS60 transcripts showed GFP expression while 5% of cells transfected with uncapped transcripts showed GFP expression. These experiments were repeated with higher amounts of uncapped inoculum. In this case a higher proportion of cells, >30% were found to be infected at this time with uncapped transcripts, where >90% of cells infected with greater amounts of capped transcripts were scored infected.

These results indicate that, contrary to the practiced art in scientific literature and in issued patents (Ahlquist et al., U.S. Pat. No. 5,466,788), uncapped transcripts for virus expression vectors are infective on both plants and in plant cells, however with much lower specific infectivity. Therefore, capping is not a prerequisite for establishing an infection of a virus expression vector in plants; capping just increases the efficiency of infection. This reduced efficiency can be overcome, to some extent, by providing excess in vitro transcription product in an infection reaction for plants or plant cells.

The expression of the 30 K movement protein of TMV in transgenic plants also has the unexpected effect of equalizing the relative specific infectivity of uncapped verses capped transcripts. The mechanism behind this effect is not fully understood, but could arise from the RNA binding activity of the movement protein stabilizing the uncapped transcript in infected cells from prereplication cytosolic degradation.

Extra guanine residues located between the T7 promoter and the first base of a virus cDNA lead to increased amount of RNA transcript as predicted by previous work with phage polymerases. These polymerases tend to initiate more efficiently at . . . TATAGG or . . . TATAGGG than . . . TATAG. This has an indirect effect on the relative infectivity of uncapped transcripts in that greater amounts are synthesized per reaction resulting in enhanced infectivity.

Data Concerning Cap Dependent Transcription of pBTI 1056 GTN#28

TMV-based virus expression vector pBTI 1056 GTN#28 which contains the T7 promoter (underlined) followed GTC bases (bold) then the virus cDNA sequence ( . . . TATAGTCGTATT . . . )(SEQ ID NO:21). This expression vector expresses the cycle 3 shuffled green fluorescent protein (GFPc3) in localized infection sites and systemically infected tissue of infected plants. This vector was transcribed in vitro in the presence (capped) and absence (uncapped) of cap analogue. Transcriptions were mixed with abrasive and inoculated on expanded older leaves of a wild type *Nicotiana benthamiana* (Nb) plant and a Nb plant expressing a TMV U1 30 k movement protein transgene (Nb 30 K). Four days post inoculation (dpi) long wave UV light was used to judge the number of infection sites on the inoculated leaves of the plants. Systemic, non-inoculated tissues, were monitored from 4 dpi on for appearance of systemic infection indicating vascular movement of the inoculated virus. Table 2 shows data from two representative experiments at 11 dpi.

TABLE 2

| Construct | Local infection sites | | Systemic Infection | |
| --- | --- | --- | --- | --- |
| | Nb | Nb 30K | Nb | Nb 30K |
| Experiment 1 pBTI1056 GTN#28 | | | | |
| Capped | 18 | 25 | yes | yes |
| Uncapped | 2 | 4 | yes | yes |
| Experiment 2 pBTI1056 GTN#28 | | | | |
| Capped | 8 | 12 | yes | yes |
| Uncapped | 3 | 5 | yes | yes |

These data further support the utility of uncapped transcripts to initiate infections by plant virus expression vectors and further demonstrates that the introduction of extra, non-viral nucleotides at the 5'-end of in vitro transcripts does not preclude infectivity of uncapped transcripts.

Example 4
Expressing Sequence Libraries to Select Genetic Stability of Foreign Genes Insertion of foreign gene sequences into virus expression vectors can result in arrangements of sequences that interfere with normal virus function and thereby, establish a selection landscape that favors the genetic deletion of the foreign sequence. Such events are adverse to the use of such expression vectors to stably express gene sequences systemically in plants. A method that would allow sequences to be identified that may insulate functional virus sequences from the potential adverse effects of insertion of foreign gene sequences would greatly augment the expression potential of virus expression vectors. In addition, identification of such "insulating" sequences that simultaneously enhanced the translation of the foreign gene product or the stability of the MRNA encoding the foreign gene would be quite helpful. The example below demonstrates how libraries of random sequences can be introduced into virus vectors flanking foreign gene sequences. Upon analysis, a subset of introduced sequences allowed a foreign gene sequence that was previously prone to genetic deletion to remain stably in the virus vectors upon serial passage. The use of undefined sequences to enhance the stability of foreign gene sequences can be extrapolated to the use of undefined sequences to enhance the translation of foreign genes and the stability of coding mRNAs by those skilled in the art.

Undefined sequences can also be used to enhance and extend the expression of foreign genes in a viral vector. To test this hypothesis random sequences of N20 were cloned in-between the TMV subgenomic promoter and the gene sequence for either human growth hormone (hGH) or a ubiquitin-hGH fusion gene. In this experiment the site of random nucleotide insertion was following a PacI (underlined) restriction enzyme site in the virus vector. This sequence is known as a leader sequence and has been derived from the native leader and coding region from the native TMV U1 coat protein gene. In this leader, the normal coat protein ATG has been mutated to a Aga sequence (underlined in GTTTTAAATAgaTCTTACAGTATCAC-TACTCCATCTCAGTTCGTGTTCTTGT CA<u>TTAATTAA</u> ATG . . . (SEQ ID NO:22hGH GENE)). A particular subset of this leader sequence (TCTTACAGTATC ACTACTCCATCTCAGTTCGTGTTCTTGTCA) (SEQ ID NO:23) has been known to increase genetic stability and gene expression when compared with virus construct lacking the leader sequence. The start site of subgenomic RNA synthesis is found at the GTTTT . . . An oligonucleotide RL-1 (GTTTTAAATAGATCTTAC N(20) TTAATTAAGGCC) (SEQ ID NO:24) was used with a primer homologous to the NcoI/ApaI region of the TMV genome to amplify a portion of the TMV movement protein. The population of sequences were cloned into the ApaI and PacI sites of the p30B hGH vector. Vectors containing the undefined sequences leading the hGH genes were transcribed and inoculated onto *Nicotiana benthamiana* plants. Fourteen days post inoculation, systemic leaves were ground and the plant extracts were inoculated onto a second set of plants. Following the onset of virus symptoms in the second set of plants, Western blot analysis was used to detect if hGH or Ubiq-hGH fusions were present in the serially inocuated plants. Several variants containing novel sequences in the non-translated leader sequence were associated with viruses that expressed higher than control levels of hGH or Ubiquitin hGH fusion proteins in plants inoculated with in vitro synthesized transcripts or upon serial passage of virus. The sequence surrounding the leader was determined and compared with that of the control virus vectors.

either express the greatest level of fluorescence or cells that survive the highest amount of herbicide. In this manner the cells with the viruses with the highest foreign gene activity would be then purified and characterized by sequencing and more thorough analysis such as Northern and Western blotting to access the stability of the mRNA and the abundance of the foreign gene of interest.

Example 5

Method for Using Reporter Genes Fused to Regulated or Constitutive Promoters as a Surrogate Marker for Identifying Genes Impacting Gene Regulation In this example we show 1) a method to construct transgenic hosts expressing a reporter gene under the control of various promoter types; 2) means to use such hosts to identify genes from libraries expressed in virus expression vectors that alter gene regulation.

The initial construction of the reporter gene expression cassette will require identification of the appropriate reporter gene, which could include GFP (fluorescent in live plants under long wave UV light), GUS (fluorescent and color-based assay in detected tissue), herbicide resistance genes (live or death phenotype upon treatment with herbicide) or

```
p30B #5 HGH      GTTTTAAATAGATCTTAC--TATAACATGAATAGTCATCG (SEQ ID NO:25)

p30B #5 HGH      GTTTTAAATAGATCTTAC--TATACCATGAATTAGTACCG (SEQ ID NO:26)

p30B #6 UbiqHGH  GTTTTAAATAGATCTTAC--ACTCGGTTGAGATAAAACTAAACTA (SEQ ID NO:27)

p30B #2 HGH      GTTTTAAATAGATCTTAC--TCCGACGTATAGTCACCACG (SEQ ID NO:28)

p30B HGH         GTTTTAAATAGATCTTAC--AGTATCACTACTCCATCTCAGTTCGTGTTCT (SEQ ID NO:29)

p30BUbiqHGH      GTTTTAAATAGATCTTAC--AGTATCACTACTCCATCTCAGTTCGTGTTCT (SEQ ID NO:30)
                 ****************** p30B #5 HGH        ---TTAATTAAAATGGGA--(SEQ ID NO:31)

p30B #5 HGH        ---TTAATTTAAAATGGGAAAAAATGGCTTCTCTATTTGCCACATTTTTA (SEQ ID NO:32)

p30B #6 UbiqHGH    ---TTAATTAAAATGGGAAAAAATGGCTCTCTTATTGGCCCCATTTTAT (SEQ ID NO:33)

p30B #2 HGH        ---TTAATTAAAAATGCAGATTTFCGTCAAGACTTTGACCGGG (SEQ ID NO:34)

p30B HGH         TGTCATTAATTAAAATGGGAAAAAATGGCTTCTCTATTTGCCACATTTTTA (SEQ ID NO:35)

p30B UbiqHGH     TGTCATTAATTAAAATGCAGATTTTCGTCAAGACTTTGACCGGT (SEQ ID NO:36)
                      ************
```

* indicates sequences that are identical in all viruses.
-- indicates end of defined primer and start of N(20) region of the oligonucleotide that was introduced during PCR amplification.

The result was that undefined leader constructs transcribed were passageable as virus. The nature of the random leaders indicates that each are unique and that multiple solutions are readily available to solve RNA based stability problems. Likewise, such random sequence introductions could also increase the translational efficiency.

In order to select for undefined sequences that may increase the translational efficiency of foreign genes or increases the stability of the mRNA encoding the foreign gene derived from a virus expression vector, a selectable marker could be used to discover which of the undefined sequences yield the desired function. The amount of the GFP protein correlates with the level of fluorescence seen under long wave UV light and the amount of herbicide resistance gene product correlates with survival of plant cells or plants upon treatment with the herbicide. Therefore introduction of undefined sequences surrounding the GFP or herbicide resistance genes and then screening for individual viruses that other scoreable gene products known to the art. Promoter sequences can express RNA in constitutive or induced conditions. An example of a regulated promoter would be that of tomato or potato protease inhibitor type I gene (Graham, et al., *J. Biol. Chem.* 260:6555–6560 (1985)). These promoters are up regulated in the presence of jasmonic acid or herbivore damage to plant tissues. Constitutive promoters are readily identifiable from anyone skilled in the art inspecting the relevant literature. Such combinations of inducible or constitutive promoters using appropriate reporter genes would be integrated into binary plant transformation vectors, transformed into Agrobacterium and transformed into *Nicotiana benthamiana* leaf disks. Upon identification of the appropriate gene construct in regenerated tissues, the primary transformants would be shelved to obtain the first stable line of plants for assay.

Libraries of cDNAs, full-length for gene overexpression or gene fragments for sense or anti-sense based gene suppression, would be ligated into virus expression vectors by normal molecular biology techniques. These libraries would be prepared for inoculation by the methods described in this patent application. Once inoculated, hosts with inducible promoters fused to reporter genes, maintained in uninduced state, would be monitored for aberrant expression of the reporter gene in tissue that contains replicating virus. If hosts containing constitutive promoter fusions to reporter genes are used, monitoring for hyper- or hypo-expression conditions of the reporter gene would be the focus. In this manner, genes that augment pathways that induce or upregulate the activity of certain promoters could be identified by following the surrogate marker of reporter gene expression. Conversely, gene that down-regulate or halt reporter gene expression could be identified as products that negatively effect the activities of the promoter or signaling pathway to which it is responsive. Virus vectors containing sequences that effected reporter gene expression by overexpression or suppression positive or negative regulatory factors can be isolated, and foreign gene contained may be sequenced and analyzed by boinformatic methods.

Example 6
Method to Induce the Expression of Alternative Splicing Variants to Discover Biological Effects in Host Organisms and to use Said Host Organism as a Source for Novel cDNA Libraries Enriched for Alternatively Spliced Variants of Genes Transcription of nuclear genes in higher eukaryotic organisms results in a primary RNA transcript that contains both coding (exon) and non-coding (intron) information. A crucial step in RNA maturation before exporting to the cytosol for translation is the splicing of introns from the primary transcript and the rendering of contiguous exons for coding of the desired product. It is interesting to note that, although, splicing may occur in defined sites constitutively in certain gene, many genes can be spliced to produce multiple protein products, each with separate functions. The process of splicing out different sets of intron and splicing together of different array and order of exons for the same primary transcript is known is alternative splicing. This is powerful way genetic economy can be achieved in higher organisms to encode for multiple functions in a single gene cistron. The events of alternative splicing are regulated by families of small nuclear RNAs and associated proteins. These factors are responsible for the choice of splice sites used in primary RNA transcript and the nature of the mature MRNA reconstructed from the splicing process. Many alternative splicing events produce rare or tissue specific RNAs that result in the translation of specific protein products that have unique activities. The most famous of which is the alternative splicing of a Drosophila transcription factor results in the sex determination of the developing embryo. For a reference describing general alternative splicing, see Lopez, *Ann. Rev. Genetics*, 32:279–305 (1998).

Since alternatively spliced mRNAs encode for proteins with differing functions, it would be interesting to investigate hosts that are deficient in these factors or hosts that no longer express such factors. It is difficult to accurately and effectively represent this diversity in standard cDNA libraries constructed from unaltered eukaryotic hosts. However, the use of virus expression vectors to overexpress or suppress the expression of factors involved in the splicing process will make it possible to increase the proportion of alternatively spliced mRNA in the host organism. Focused gene libraries will be constructed for the overexpression and the sense or antisense suppression of factors with potential and actual activities in the RNA splicing process in plants. Gene families can include the SF2/ASF-like group of splicing factors (Lopato et al., *PNAS* 92:7672–7676 (1995)), the RS-rich family of splicing factors (Lapato et al., *The Plant Cell* 8:2255–2264 (1996)) and other splicing families that have been identified in the literature in lower or upper eukaryotic systems. The gene libraries will be sub-cloned into virus expression vectors and virus libraries will be inoculated as individuals or pools onto plants or plant cells. Once individual or groups of splicing factors are overexpressed or have their expression suppressed in plant cells, novel forms of splicing will occur due to the role of these proteins in alternative splicing of many transcription factors, splicing factors or other gene products. The high level of expression achieved by virus expression vectors and their ability to infect most cell types in plants should raise the overall level of aberrantly expressed mRNAs in the plant. The transfected plants will be used as the starting point for the isolation of poly A(+) RNA for the construction of cDNAs enriched for alternatively spliced genes. The alterations in the alternative splicing could be the splicing of a greater or lesser number of introns from the primary mRNA than normally occurs in non-transfected plants. These enriched cDNA libraries can now be cloned into virus expression vectors and the functions of these novel spliced forms of genes can be assayed on plants transfected with these vector libraries.

In this example, one can discover the plietropic functions of factors effecting alternative or normal splicing functions in plants from primary directed virus libraries with original splicing factor genes, or from virus libraries derived from plants containing induced novel spliced mRNAs.

Similar methods could be to derive novel cDNA libraries by using virus vectors to express factors responsible for transcriptional regulation of genes in plants. In this example, targeted cloning of transcription factor families would be ligated into virus expression vectors. Families could include homeodomain, Zn finger, leucine zipper and other transcription factor families appearing in pro or eukaryotic genomes. Schwechheimer, et al., *Ann. Rev. Plant Phys. and Plant Mol. Biol.* 49:127–150 (1998). The gene libraries will be sub-cloned into virus expression vectors and virus libraries will be inoculated as individuals or pools onto plants or plant cells. Once individual or groups of transcription factors are overexpressed or have their expression suppressed in plant cells or plants, novel patterns of gene expression patterns will be induced. This will result in the appearance of a higher proportion of cDNAs normally present at low levels in the plant tissue or that are normally developmentally regulated. However, with the high level of expression achieved by virus expression vectors and their ability to infect most cell types in plants should induce these tissue specific cDNAs in aberrant cell types and at much higher than normal levels. The transfected plants will be used as the starting point for the isolation of poly A(+) RNA for the construction of cDNAs enriched for alternatively lowly expressed or developmentally expressed cDNAs. These cDNAs would be used to construct expression or gene suppression libraries that will be enriched for these rare or aberrantly expressed cDNAs. These enriched cDNA libraries can now be cloned into virus expression vectors and the functions of these novel spliced forms of genes can be assayed on plants transfected with these vector libraries.

Example 7
Composite Cloning to Facilitate Cloning of Libraries in Virus Vectors and/or Their Introduction into Host Cells for Expression of Sequences This example shows an alternative method for facilitating the expression of viral nucleic acid sequence libraries. Virus vector clones could be integrated into lambda phage or cosmid clones to facilitate library construction, clone representation, elimination of cell based amplification by direct transcription and archiving of individual clones. Likewise, cis-acting elements allowing for expression in plant cells or integration into plant DNA could be included into such plasmids to facilitate inoculation of DNA for direct expression, obviating the need for transcription of vector cDNA, or construction of dedicated plant transformation vectors.

Virus vectors are tools housing libraries of sequences that can be screened for novel gene discovery. Libraries are often first constructed in plasmid or phage shuttle vectors before excising and introduction into virus vectors. Likewise, sequences can be screened in hosts using virus vectors, but must be subcloned into appropriate eukaryotic expression vectors before the trait identified in the vector transfected host will become a stable trait in the host by gene integration. Additional steps involve: (1) construction of libraries to most efficiently represent the clones in a cDNA library, (2) obtaining maximal transfection efficiency into bacterial hosts (if used), and (3) archiving DNA samples without the need for transfection into bacteria and transcription of ligated DNA. The integration of a virus vector into a cosmid clone, or lambda phage itself, (both termed phagmids here) could allow a multi-purpose vector to be generated to be both the repository of primary generated library sequences, source for ligation transcriptions, high efficiency bacterial transfection and direct expression in higher eukaryotic hosts. Using normal cloning procedures, the 5' half of the virus vector to be inserted into one arm of a phagmid DNA clone with a non symmetrical restriction (such as BstXI: CCANNNNNNTGG) (SEQ ID NO:37) containing a unique sticky sequence (the N's). The 3' part of the vector will be inserted into another arm with a non-symmetrical restriction (such as BstXI: CCANNNNNNTGG) (SEQ ID NO:37) containing a second unique sticky sequence (the N's). The vector would be split at the determined restriction site (e.g. BstXI) within the site for foreign sequence expression in the virus vector. The 5'-end of the virus cDNA would be appropriately fused to a promoter for in vitro transcription (e.g. T7) or for in vivo expression (e.g. an appropriate higher eukaryotic RNA polymerase promoter). The 3'-end of the virus cDNA would terminate with a ribozyme for in vitro cleavage and/or a 3' terminator from a gene from host organism to lead to in vivo termination of transcription. Left and right T-DNA borders that promote the integration of sequences in between into plant genomic DNA, could flank the promoter and terminator sequences. At the terminus of each arm would be cos sequences to allow complete regeneration of the phagmid upon ligation in the presence of foreign library DNA containing the two unique sticky sequences at each respective termini. These library DNA fragments could be generated by PCR amplification using determined restriction sites (e.g., BstXI) to generate unique sticky ends complementary to those in the phagmid-vector arms integrated in the PCR primers. The 5' and 3' primers would each have unique recognition sequences in the BstXI restriction site (the N's) that would match the sticky sites on the respective sides of the virus vector. The sites could be switched on a second set of PCR primers to allow the amplification of DNA to be ligated into the phagmid-viral vector arms in the "sense" and "anti-sense" orientation. These constructions would allow for efficient in vitro ligation and use of crude ligation mix as template for *E. coli* transformation, plant transformation, in vitro lambda packaging to $10^9$ pfu/mcg or in vitro transcription. In this manner, the vector and flexibility for its screening could be maximized. These tools we can directly build complex libraries into and simultaneously be the enabling tool for analysis.

Although the foregoing invention has been described in some detail by way of illustration and example for purposes of clarity of understanding, it will be obvious that certain changes and modifications may be practiced within the scope of the appended claims.

All publications, patents, patent applications are herein incorporated by reference in their entirety to the same extent as if each individual publication, patent, or patent application was specifically and individually indicated to be incorporated by reference in its entirety.

We claim:

1. A method for screening for a trait comprising the steps of:
 (a) introducing a nucleic acid library comprising nucleic acid sequence variants of a template nucleic acid sequence into a viral vector, wherein the number of sequence variants in the library is at least about 64;
 (b) transiently expressing the nucleic acid library in a plant host;
 (c) detecting changes resulting from the expression of the nucleic acid library; and
 (d) repeating steps (a)–(c), if necessary, with successively less number of sequence variants until at least one sequence in the nucleic acid library confers said trait.

2. The method according to claim 1 further comprising the step of (e) sequencing said at least one sequence.

3. The method according to claim 1 wherein said nucleic acid library contains random nucleic acid sequence variants.

4. The method according to claim 1 wherein said nucleic acid library contains known nucleic acid sequence variants.

5. The method according to claim 1 wherein said nucleic acid library is generated by in vitro mutagenesis or recombination.

6. The method according to claim 1 wherein said nucleic acid library is constructed in cell free manner.

7. The method according to claim 1 wherein said nucleic acid library is native to an RNA plant virus.

8. The method of claim 1 wherein said nucleic acid library is native to a single-stranded, plus sense RNA plant virus.

9. The method according to claim 1 wherein said trait comprises movement activity.

10. The method according to claim 1 wherein said trait comprises promoter activity.

11. The method according to claim 1 wherein said trait comprises host range.

12. The method according to claim 1 wherein said trait comprises signaling activity.

13. The method according to claim 1 wherein said trait comprises replication activity.

14. The method according to claim 1 wherein said trait comprises translation activity.

15. The method according to claim 1 wherein said changes are biochemical.

16. The method according to claim 1 wherein said changes are phenotypic.

17. The method of claim 16 wherein the phenotypic changes are in color or morphology.

18. The method according to claim 1 wherein said template nucleic acid sequence is native to a viral nucleic acid.

19. The method according to claim 18 wherein said template nucleic acid sequence encodes a movement protein or fragments thereof.

20. The method according to claim 18 wherein said template nucleic acid sequence is a promoter sequence or fragments thereof.

21. The method according to claim 18 wherein said template nucleic acid sequence encodes a coat protein or fragments thereof.

22. The method according to claim 18 wherein said template nucleic acid sequence is a ribosomal sequence or fragments thereof.

23. The method according to claim 1 wherein said template nucleic acid sequence is non-native to viral nucleic acids.

24. The method according to claim 23 wherein said template nucleic acid sequence encodes a non-native polypeptide.

25. The method according to claim 23 wherein said template nucleic acid sequence is a non-native regulatory sequence.

* * * * *

SEQUENCE LISTING

```
<160> NUMBER OF SEQ ID NOS:  37

<210> SEQ ID NO 1
<211> LENGTH: 87
<212> TYPE: DNA
<213> ORGANISM: Tobacco mosaic virus

<400> SEQUENCE: 1 agt ttg ttt ata gat ggc tct agt tgt taa atagatctta cagtatcact      50
actccatctc agttcgtgtt cttgtcatta ataaatg                          87

<210> SEQ ID NO 2
<211> LENGTH: 9
<212> TYPE: PRT
<213> ORGANISM: Tobacco mosaic virus

<400> SEQUENCE: 2

Ser Leu Phe Ile Asp Gly Ser Ser Cys
1               5
```

```
<210> SEQ ID NO 3
<211> LENGTH: 11
<212> TYPE: PRT
<213> ORGANISM: Tobacco mosaic virus

<400> SEQUENCE: 3

Met Ala Leu Val Val Lys Gly Lys Asp Ser Phe
 1               5                  10

<210> SEQ ID NO 4
<211> LENGTH: 55
<212> TYPE: DNA
<213> ORGANISM: Tobacco mosaic virus

<400> SEQUENCE: 4 agt ttg ttt ata gac ggc tct agt tgt taa gcctaggagc cggcttaatt      50
aaatg                                                              55

<210> SEQ ID NO 5
<211> LENGTH: 9
<212> TYPE: PRT
<213> ORGANISM: Tobacco mosaic virus

<400> SEQUENCE: 5

Ser Leu Phe Ile Asp Gly Ser Ser Cys
 1               5

<210> SEQ ID NO 6
<211> LENGTH: 117
<212> TYPE: DNA
<213> ORGANISM: Tobacco mosaic virus

<400> SEQUENCE: 6 agt ttg ttt ata gat ggc tct agt tgt taa g atggctctag ttgttaaagg    51
agttttaaat agatcttaca gtatcactac tccatctcag ttcgtgttct tgtcattaat  111
taaatg                                                             117

<210> SEQ ID NO 7
<211> LENGTH: 9
<212> TYPE: PRT
<213> ORGANISM: Tobacco mosaic virus

<400> SEQUENCE: 7

Ser Leu Phe Ile Asp Gly Ser Ser Cys
 1               5

<210> SEQ ID NO 8
<211> LENGTH: 8
<212> TYPE: PRT
<213> ORGANISM: Tobacco mosaic virus

<400> SEQUENCE: 8

Met Ala Leu Val Val Lys Gly Lys
 1               5

<210> SEQ ID NO 9
<211> LENGTH: 29
<212> TYPE: DNA
<213> ORGANISM: Tobamovirus

<400> SEQUENCE: 9
ggccctagga tggctctagt tgttaaagg                                    29
```

```
<210> SEQ ID NO 10
<211> LENGTH: 34
<212> TYPE: DNA
<213> ORGANISM: Tobamovirus

<400> SEQUENCE: 10
gttcttctcc tttgctagcc atttaattaa tgac                                    34

<210> SEQ ID NO 11
<211> LENGTH: 11
<212> TYPE: DNA
<213> ORGANISM: Tobacco mosaic virus

<400> SEQUENCE: 11
tatagtattt t                                                             11

<210> SEQ ID NO 12
<211> LENGTH: 11
<212> TYPE: DNA
<213> ORGANISM: Tobacco mosaic virus

<400> SEQUENCE: 12
tataggtatt t                                                             11

<210> SEQ ID NO 13
<211> LENGTH: 11
<212> TYPE: DNA
<213> ORGANISM: Tobacco mosaic virus
<220> FEATURE:
<221> NAME/KEY: misc_feature
<222> LOCATION: (6)...(6)
<223> OTHER INFORMATION: N = A,T,C, or G

<400> SEQUENCE: 13
tatagntatt t                                                             11

<210> SEQ ID NO 14
<211> LENGTH: 13
<212> TYPE: DNA
<213> ORGANISM: Tobacco mosaic virus
<220> FEATURE:
<221> NAME/KEY: misc_feature
<222> LOCATION: (7)...(7)
<223> OTHER INFORMATION: N = A,T,C, or G

<400> SEQUENCE: 14
tatagtngta ttt                                                           13

<210> SEQ ID NO 15
<211> LENGTH: 12
<212> TYPE: DNA
<213> ORGANISM: Nicotiana benthamiana

<400> SEQUENCE: 15
tataggtatt tt                                                            12

<210> SEQ ID NO 16
<211> LENGTH: 14
<212> TYPE: DNA
<213> ORGANISM: Nicotiana benthamiana

<400> SEQUENCE: 16
tatagtcgta tttt                                                          14
```

```
<210> SEQ ID NO 17
<211> LENGTH: 15
<212> TYPE: DNA
<213> ORGANISM: Nicotiana benthamiana
<220> FEATURE:
<221> NAME/KEY: misc_feature
<222> LOCATION: (7)...(10)
<223> OTHER INFORMATION: N = A,T,C, or G

<400> SEQUENCE: 17
tatagtngtn gtatt                                                15

<210> SEQ ID NO 18
<211> LENGTH: 21
<212> TYPE: DNA
<213> ORGANISM: Nicotiana benthamiana
<220> FEATURE:
<221> NAME/KEY: misc_feature
<222> LOCATION: (7)...(16)
<223> OTHER INFORMATION: N = A,T,C, or G

<400> SEQUENCE: 18
tatagtngtn gtngtngtat t                                         21

<210> SEQ ID NO 19
<211> LENGTH: 16
<212> TYPE: DNA
<213> ORGANISM: Nicotiana benthamiana

<400> SEQUENCE: 19
tatagtattt gtattt                                               16

<210> SEQ ID NO 20
<211> LENGTH: 10
<212> TYPE: DNA
<213> ORGANISM: Nicotiana benthamiana

<400> SEQUENCE: 20
tataggtatt                                                      10

<210> SEQ ID NO 21
<211> LENGTH: 12
<212> TYPE: DNA
<213> ORGANISM: Tobacco mosaic virus

<400> SEQUENCE: 21
tatagtcgta tt                                                   12

<210> SEQ ID NO 22
<211> LENGTH: 65
<212> TYPE: DNA
<213> ORGANISM: Tobacco mosaic virus

<400> SEQUENCE: 22
gttttaaata gatcttacag tatcactact ccatctcagt tcgtgttctt gtcattaatt    60
aaatg                                                           65

<210> SEQ ID NO 23
<211> LENGTH: 42
<212> TYPE: DNA
<213> ORGANISM: Tobacco mosaic virus

<400> SEQUENCE: 23
tcttacagta tcactactcc atctcagttc gtgttcttgt ca                  42
```

```
<210> SEQ ID NO 24
<211> LENGTH: 31
<212> TYPE: DNA
<213> ORGANISM: Tobacco mosaic virus
<220> FEATURE:
<221> NAME/KEY: misc_feature
<222> LOCATION: (19)...(19)
<223> OTHER INFORMATION: N = A,T,C, or G

<400> SEQUENCE: 24
gttttaaata gatcttacnt taattaaggc c                                31

<210> SEQ ID NO 25
<211> LENGTH: 38
<212> TYPE: DNA
<213> ORGANISM: Nicotiana benthamiana

<400> SEQUENCE: 25
gttttaaata gatcttacta taacatgaat agtcatcg                         38

<210> SEQ ID NO 26
<211> LENGTH: 38
<212> TYPE: DNA
<213> ORGANISM: Nicotiana benthamiana

<400> SEQUENCE: 26
gttttaaata gatcttacta taccatgaat tagtaccg                         38

<210> SEQ ID NO 27
<211> LENGTH: 43
<212> TYPE: DNA
<213> ORGANISM: Nicotiana benthamiana

<400> SEQUENCE: 27
gttttaaata gatcttacac tcggttgaga taaaactaaa cta                   43

<210> SEQ ID NO 28
<211> LENGTH: 38
<212> TYPE: DNA
<213> ORGANISM: Nicotiana benthamiana

<400> SEQUENCE: 28
gttttaaata gatcttactc cgacgtatag tcaccacg                         38

<210> SEQ ID NO 29
<211> LENGTH: 49
<212> TYPE: DNA
<213> ORGANISM: Nicotiana benthamiana

<400> SEQUENCE: 29
gttttaaata gatcttacag tatcactact ccatctcagt tcgtgttct             49

<210> SEQ ID NO 30
<211> LENGTH: 49
<212> TYPE: DNA
<213> ORGANISM: Nicotiana benthamiana

<400> SEQUENCE: 30
gttttaaata gatcttacag tatcactact ccatctcagt tcgtgttct             49

<210> SEQ ID NO 31
<211> LENGTH: 15
<212> TYPE: DNA
```

```
<213> ORGANISM: Nicotiana benthamiana

<400> SEQUENCE: 31
ttaattaaaa tggga                                             15

<210> SEQ ID NO 32
<211> LENGTH: 46
<212> TYPE: DNA
<213> ORGANISM: Nicotiana benthamiana

<400> SEQUENCE: 32
ttaatttaaa atgggaaaaa tggcttctct atttgccaca tttta            46

<210> SEQ ID NO 33
<211> LENGTH: 45
<212> TYPE: DNA
<213> ORGANISM: Nicotiana benthamiana

<400> SEQUENCE: 33
ttaattaaaa tgggaaaaat ggctctctta ttggccccat tttta            45

<210> SEQ ID NO 34
<211> LENGTH: 40
<212> TYPE: DNA
<213> ORGANISM: Nicotiana benthamiana

<400> SEQUENCE: 34
ttaattaaaa atgcagattt tcgtcaagac tttgaccggg                  40

<210> SEQ ID NO 35
<211> LENGTH: 50
<212> TYPE: DNA
<213> ORGANISM: Nicotiana benthamiana

<400> SEQUENCE: 35
tgtcattaat taaatgggaa aaatggctt ctctatttgc cacattttta        50

<210> SEQ ID NO 36
<211> LENGTH: 44
<212> TYPE: DNA
<213> ORGANISM: Nicotiana benthamiana

<400> SEQUENCE: 36
tgtcattaat taaaatgcag attttcgtca agactttgac cggt             44

<210> SEQ ID NO 37
<211> LENGTH: 12
<212> TYPE: DNA
<213> ORGANISM: Tobacco mosaic virus
<220> FEATURE:
<221> NAME/KEY: misc_feature
<222> LOCATION: (4)...(11)
<223> OTHER INFORMATION: N = A,T,C, or G

<400> SEQUENCE: 37
ccannnnnnt gg                                                12
```